United States Patent
Yan et al.

(10) Patent No.: US 11,654,104 B2
(45) Date of Patent: *May 23, 2023

(54) USE OF IL-22 DIMER IN MANUFACTURE OF A MEDICAMENT FOR INTRAVENOUS ADMINISTRATION

(71) Applicant: Evive Biotechnology (Shanghai) Ltd, Shanghai (CN)

(72) Inventors: Xiaoqiang Yan, Shanghai (CN); Cheng Huang, Shanghai (CN); Dongdong Wu, Shanghai (CN); Kaiyang Tang, Shanghai (CN); Yuliang Huang, Shanghai (CN)

(73) Assignee: Evive Biotechnology (Shanghai) Ltd, Shanghai (CN)

( * ) Notice: Subject to any disclaimer, the term of this patent is extended or adjusted under 35 U.S.C. 154(b) by 346 days.

This patent is subject to a terminal disclaimer.

(21) Appl. No.: 16/709,833

(22) Filed: Dec. 10, 2019

(65) Prior Publication Data

US 2020/0155448 A1    May 21, 2020

Related U.S. Application Data

(63) Continuation of application No. 15/034,859, filed as application No. PCT/CN2014/090520 on Nov. 6, 2014, now Pat. No. 10,543,169.

(30) Foreign Application Priority Data

Nov. 7, 2013    (CN) .......................... 201310549838.1

(51) Int. Cl.
 *A61K 38/20*    (2006.01)
 *C07K 14/54*    (2006.01)
 *A61K 9/00*     (2006.01)

(52) U.S. Cl.
 CPC ............ *A61K 9/0019* (2013.01); *A61K 38/20* (2013.01); *C07K 14/54* (2013.01)

(58) Field of Classification Search
 None
 See application file for complete search history.

(56) References Cited

U.S. PATENT DOCUMENTS

| | | | |
|---|---|---|---|
| 4,179,337 A | 12/1979 | Davis et al. |
| 4,301,144 A | 11/1981 | Iwashita et al. |
| 4,399,216 A | 8/1983 | Axel et al. |
| 4,496,689 A | 1/1985 | Mitra |
| 4,640,835 A | 2/1987 | Shimizu et al. |
| 4,657,760 A | 4/1987 | Kung et al. |
| 4,670,417 A | 6/1987 | Iwasaki et al. |
| 4,683,195 A | 7/1987 | Mullis et al. |
| 4,683,202 A | 7/1987 | Mullis |
| 4,791,192 A | 12/1988 | Nakagawa et al. |
| 4,849,227 A | 7/1989 | Cho |
| 4,943,529 A | 7/1990 | Van den Berg et al. |
| 4,965,188 A | 10/1990 | Mullis et al. |
| 5,010,182 A | 4/1991 | Brake et al. |
| 5,206,344 A | 4/1993 | Katre et al. |
| 5,225,212 A | 7/1993 | Martin et al. |
| 5,428,130 A | 6/1995 | Capon et al. |
| 5,500,362 A | 3/1996 | Robinson |
| 5,624,821 A | 4/1997 | Winter |
| 5,648,260 A | 7/1997 | Winter |
| 5,654,010 A | 8/1997 | Johnson et al. |
| 5,821,337 A | 10/1998 | Carter |
| 6,194,551 B1 | 2/2001 | Idusogie |
| 6,274,710 B1 | 8/2001 | Dumoutier et al. |
| 6,306,908 B1 | 10/2001 | Carlson et al. |
| 6,331,613 B1 | 12/2001 | Dumoutier et al. |
| 6,359,117 B1 | 3/2002 | Dumoutier et al. |
| 6,551,799 B2 | 4/2003 | Gurney et al. |
| 6,737,056 B1 | 5/2004 | Presta |
| 6,797,493 B2 | 9/2004 | Sun et al. |
| 7,226,591 B2 | 6/2007 | Gurney et al. |
| 7,307,161 B1 | 12/2007 | Jacobs et al. |
| 7,332,581 B2 | 2/2008 | Presta |
| 7,371,826 B2 | 5/2008 | Presta |
| 7,459,533 B2 | 12/2008 | Jacobs et al. |
| 7,585,646 B2 | 9/2009 | Jacobs et al. |
| 7,651,694 B2 | 1/2010 | Lee |

(Continued)

FOREIGN PATENT DOCUMENTS

| CA | 2695734 A1 | 2/2009 |
|---|---|---|
| CA | 2705007 A1 | 5/2009 |

(Continued)

OTHER PUBLICATIONS

Xin et al International Immunopharmacology, 2015, vol. 28, pp. 1076-1083.*

(Continued)

*Primary Examiner* — Bridget E Bunner
*Assistant Examiner* — Fozia M Hamud
(74) *Attorney, Agent, or Firm* — Morrison & Foerster LLP

(57) ABSTRACT

The present application provides methods of administering an IL-22 dimer to an individual, such as a human individual, comprising intravenously administering to the individual an effective amount of an IL-22 dimer, wherein the amount of the IL-22 dimer is about 2 μg/kg to about 200 μg/kg (such as about 10 μg/kg to about 45 μg/kg), as well as methods of treating diseases by following such administration methods. Also provided are kits, unit dosages, and articles of manufacture for use in any one of the methods described herein.

19 Claims, 5 Drawing Sheets

Specification includes a Sequence Listing.

(56) References Cited

U.S. PATENT DOCUMENTS

| | | |
|---|---|---|
| 7,666,402 B2 | 2/2010 | Huang et al. |
| 7,696,158 B2 | 4/2010 | Huang et al. |
| 7,718,604 B2 | 5/2010 | Huang et al. |
| 7,972,833 B2 | 7/2011 | Dumoutier et al. |
| 7,981,448 B2 | 7/2011 | Otterbein et al. |
| 8,048,984 B2 | 11/2011 | Jacobs et al. |
| 8,178,082 B2 | 5/2012 | Gurney et al. |
| 8,178,675 B2 | 5/2012 | Romantsev et al. |
| 8,945,528 B2 | 2/2015 | Yan et al. |
| 8,956,605 B2 | 2/2015 | Huang et al. |
| 8,980,949 B2 | 3/2015 | Bar-yosef et al. |
| 9,352,024 B2 | 5/2016 | Wu et al. |
| 9,629,898 B2 | 4/2017 | Yan et al. |
| 10,087,227 B2 | 10/2018 | Scheer et al. |
| 10,160,793 B2 | 12/2018 | Scheer et al. |
| 10,543,169 B2 | 1/2020 | Yan et al. |
| 10,786,551 B2 | 9/2020 | Huang et al. |
| 2001/0023070 A1 | 9/2001 | Ebner et al. |
| 2002/0102723 A1 | 8/2002 | Gurney et al. |
| 2003/0100076 A1 | 5/2003 | Gurney et al. |
| 2003/0186387 A1 | 10/2003 | Ebner et al. |
| 2003/0235561 A1 | 12/2003 | Vandenburgh et al. |
| 2004/0258623 A1 | 12/2004 | Xu et al. |
| 2005/0014934 A1 | 1/2005 | Hinton et al. |
| 2005/0148029 A1 | 7/2005 | Buechler et al. |
| 2007/0172457 A1 | 7/2007 | Ebner et al. |
| 2007/0207943 A1 | 9/2007 | Ebner et al. |
| 2008/0031882 A1 | 2/2008 | Liang et al. |
| 2008/0069798 A1 | 3/2008 | Huang et al. |
| 2008/0069799 A1 | 3/2008 | Huang et al. |
| 2008/0138314 A1 | 6/2008 | Huang et al. |
| 2008/0241246 A1 | 10/2008 | Sakthivel et al. |
| 2008/0293629 A1 | 11/2008 | Rosen et al. |
| 2009/0202475 A1 | 8/2009 | Abbas et al. |
| 2009/0221008 A1 | 9/2009 | Yu et al. |
| 2010/0015086 A1 | 1/2010 | Huang et al. |
| 2010/0255508 A1 | 10/2010 | Gelzleichter et al. |
| 2011/0091417 A1 | 4/2011 | Gurney et al. |
| 2011/0262385 A1 | 10/2011 | Huang et al. |
| 2011/0268696 A1 | 11/2011 | Huang et al. |
| 2011/0280828 A1 | 11/2011 | Abbas et al. |
| 2013/0171100 A1 | 7/2013 | Yan et al. |
| 2014/0314711 A1 | 10/2014 | Scheer et al. |
| 2014/0377222 A1 | 12/2014 | Huang et al. |
| 2015/0147293 A1 | 5/2015 | Wu et al. |
| 2015/0202267 A1 | 6/2015 | Yan et al. |
| 2016/0263020 A1 | 9/2016 | Yan et al. |
| 2016/0271221 A1 | 9/2016 | Yan et al. |
| 2016/0287670 A1 | 10/2016 | Brink et al. |
| 2017/0088596 A1 | 3/2017 | Scheer et al. |
| 2017/0320926 A1 | 11/2017 | Scheer et al. |
| 2018/0015130 A1 | 1/2018 | Berry et al. |
| 2018/0028614 A1 | 2/2018 | Huang et al. |
| 2021/0100877 A1 | 4/2021 | Kolls et al. |
| 2021/0138038 A1 | 5/2021 | Brink et al. |

FOREIGN PATENT DOCUMENTS

| | | |
|---|---|---|
| CA | 2903587 A1 | 9/2014 |
| CN | 1264596 A | 8/2000 |
| CN | 1269718 A | 10/2000 |
| CN | 1381512 A | 11/2002 |
| CN | 1652802 A | 8/2005 |
| CN | 101168049 A | 4/2008 |
| CN | 101218254 A | 7/2008 |
| CN | 101225110 A | 7/2008 |
| CN | 102124344 A | 7/2011 |
| CN | 102380091 A | 3/2012 |
| CN | 103118699 A | 5/2013 |
| CN | 101896073 B | 11/2013 |
| CN | 104623637 A | 5/2015 |
| CN | 105143252 A | 12/2015 |
| EP | 0 036 776 A2 | 9/1981 |
| EP | 0 073 657 A1 | 3/1983 |
| EP | 0 117 058 A2 | 8/1984 |
| EP | 0 117 060 A2 | 8/1984 |
| EP | 0 139 383 A1 | 5/1985 |
| EP | 0 183 070 A2 | 6/1986 |
| EP | 0 244 234 A2 | 11/1987 |
| EP | 0 362 179 A2 | 4/1990 |
| EP | 0 394 538 A1 | 10/1990 |
| EP | 0 402 226 A1 | 12/1990 |
| EP | 1748789 B1 | 12/2010 |
| EP | 3065763 A1 | 9/2016 |
| JP | 2008-508862 A | 3/2008 |
| JP | 2011-507863 A | 3/2011 |
| JP | 2013-536254 A | 9/2013 |
| WO | WO-1987/05330 A1 | 9/1987 |
| WO | WO-1989/05859 A1 | 6/1989 |
| WO | WO-1991/00357 A1 | 1/1991 |
| WO | WO-1994/08606 A | 4/1994 |
| WO | WO-1994/29351 A2 | 12/1994 |
| WO | WO-1995/013312 A1 | 5/1995 |
| WO | WO-1995/022419 A1 | 8/1995 |
| WO | WO-1996/07399 A1 | 3/1996 |
| WO | WO-1996/34103 A1 | 10/1996 |
| WO | WO-1996/40072 A2 | 12/1996 |
| WO | WO-1997/03692 A1 | 2/1997 |
| WO | WO-1999/32139 A1 | 7/1999 |
| WO | WO-1999/51642 A1 | 10/1999 |
| WO | WO-1999/54440 A1 | 10/1999 |
| WO | WO-1999/61617 A1 | 12/1999 |
| WO | WO-2002/029098 A2 | 4/2002 |
| WO | WO-2003/013589 A1 | 2/2003 |
| WO | WO-2003/089569 A2 | 10/2003 |
| WO | WO-2004/056312 A2 | 7/2004 |
| WO | WO-2005/044292 A2 | 5/2005 |
| WO | WO-2005/100402 A1 | 10/2005 |
| WO | WO-2006/000448 A2 | 1/2006 |
| WO | WO-2006/029879 A2 | 3/2006 |
| WO | WO-2006/073508 A1 | 7/2006 |
| WO | WO-2006/088833 A2 | 8/2006 |
| WO | WO-2007/047796 A2 | 4/2007 |
| WO | WO-2007/115230 A2 | 10/2007 |
| WO | WO-2009/020844 A1 | 2/2009 |
| WO | WO-2009/041734 A1 | 4/2009 |
| WO | WO-2009/062102 A2 | 5/2009 |
| WO | WO-2009/079024 A1 | 6/2009 |
| WO | WO-2010/081112 A1 | 7/2010 |
| WO | WO-2011/087986 A1 | 7/2011 |
| WO | WO-2012/028089 A1 | 3/2012 |
| WO | WO-2013/097748 A1 | 7/2013 |
| WO | WO-2014/145016 A2 | 9/2014 |
| WO | WO-2015/067198 A1 | 5/2015 |
| WO | WO-2015/067199 A1 | 5/2015 |
| WO | WO-2015/070077 A1 | 5/2015 |
| WO | WO-2015/197861 A1 | 12/2015 |
| WO | 2016086205 A2 | 6/2016 |
| WO | WO-2019/148020 A1 | 8/2019 |
| WO | WO-2019/165140 A1 | 8/2019 |
| WO | 2021160163 A1 | 8/2021 |
| WO | WO-2021/164744 A | 8/2021 |

OTHER PUBLICATIONS

Nazanin et al, Innovations in Clinical Neuroscience; 2016, vol. 13, (7-8), pp. 30-36.*

Adachi, M. et al. (2005). "Clinical Syndromes of Alcoholic Liver Disease," Digestive Diseases 23(3-4):255-263.

Adams, L.A. et al. (2006). "Treatment of Non-Alcoholic Fatty Liver Disease," Postgrad Med J 82:315-322.

Afrazi, A. et al. (May 1, 2012, Epub Mar. 28, 2012) "Intracellular heat shock protein-70 negatively regulates TLR4 signaling in the newborn intestinal epithelium," J Immunol. 188(9):4543-4557.

Arab, J.P. et al. (e-pub Nov. 27, 2019). "An Open Label, Dose Escalation Study to Assess the Safety and Efficacy of IL-22 Agonist F-652 in Patients With Alcoholic Hepatitis," Hepatology, doi: 10.1002/hep.31046.

Arora, P. et al. (2019). "[P21] A Randomized, Multiple-Dose Study of Subcutaneous UTTR1147A (IL-22Fc) in Patients with Neuropathic, Non-Healing Diabetic Foot Ulcers (DFUs)," Journal of Diabetes Science and Technology 14(3):632.

(56) References Cited

OTHER PUBLICATIONS

Asiedu, C. et al. (2007). "Cloning and Characterization of Recombinant Rhesus Macaque IL-10/Fc(ala-ala) Fusion Protein: A Potential Adjunct for Tolerance Induction Strategies," Cytokine 40:183-192.

Asplund, S. et al. (1998). "Chronic Mucosal Changes of the Colon in Graft-versus-Host Disease," Mod Pathol 11(6): 513-515.

Aujla, S.J. et al. (Mar. 2008, e-pub. Feb. 10, 2008). "IL-22 Mediates Mucosal Host Defense Against Gram-Negative Bacterial Pneumonia," Nat Med 14(3):275-281, 7 pages.

Ballance, D.J. et al. (Apr. 15, 1983). "Transformation of *Aspergillus nidulans* by the Orotidine- 5'-Phosphate Decarboxylase Gene of Neurospora Crassa," Biochem. Biophys. Res. Commum. 112(1):284-289.

Balthazar, E.J. et al. (Feb. 1990). "Acute Pancreatitis: Value of CT in Establishing Prognosis," Radiology 174(2):331-336.

Balthazar, E.J. et al. (Sep. 1985). "Acute Pancreatitis: Prognostic Value of CT," Radiology 156(3)767-772.

Bamba, T. et al. (Aug. 2003). "Bacterial Translocation From Basic to Clinical Study," Nihon Shokakibyo Gakkai Zasshi the Japanese Journal of Gastro-Enterology 100(8):957, 9 pages. (English Abstract).

Banks, P.A. et al. (Oct. 2006). "Practice Guidelines in Acute Pancreatitis," The American Journal of Gastroenterology 101(10): 2379-2400.

Barker, N. et al. (Oct. 25, 2007, e-pub. Oct. 14, 2007). "Identification of Stem Cells in Small Intestine and Colon by Marker Gene Lgr5," Nature 449:1003-1007.

Barker, N. et al. (Oct. 5, 2012). "Identifying the Stem Cell of the Intestinal Crypt: Strategies and Pitfalls," Cell Stem Cell 11:452-460.

Beach, D. et al. (Mar. 12, 1981). "High-frequency Transformation of the Fission Yeast Schizosaccharomyces pombe," Nature 290:140-142.

Bingold, T.M. et al. (Oct. 2010). "Interleukin-22 Detected in Patients With Abdominal Sepsis," Shock 34(4):337-340.

Blazar, B. R., et al. (May 11, 2012). "Advances in Graft-Versus-Host Disease Biology and Therapy," Nat Rev Immunol 12(6):443-458, 31 pages.

Bone, R.C. et al. (Jun. 1, 1992). "Definitions for Sepsis and Organ Failure and Guidelines for the Use of Innovative Therapies in Sepsis," Chest 101:1644-1655.

Browning, J.D. et al. (Jul. 2004). "Molecular Mediators of Hepatic Steatosis and Liver Injury," The Journal of Clinical Investigation 114(2):147-152.

Bruggemann, M. et al. (Nov. 1, 1987). "Comparison of the Effector Functions of Human Immunoglobulins Using a Matched Set of Chimeric Antibodies," J. Exp. Med. 166(5):1351-1361.

Caballero, F. et al. (2009). "Enhanced Free Cholestrol, SREBP-2 and StAR Expression in Human NASH," Journal of Hepatology 50:789-796.

Carlson, M.J. et al. (Feb. 5, 2009, e-pub Oct. 28, 2008). "In vitro-Differentiated TH17 Cells Mediate Lethal Acute Graft-Versus-Host Disease With Severe Cutaneous and Pulmonary Pathologic Manifestations," Blood. 113(6):1365-1374.

Carmon, K.S. et al. (Jun. 2012; e-pub. Apr. 2, 2012). "LGR5 Interacts and Cointernalizes with Wnt Receptors to Modulate Wnt/β-Catenin Signaling," Mol Cell Biol 32(11):2054-2064.

Carryer, H.M. (Jul. 1950). "The Effect of Cortisone of Bronchial Asthma and Hay Fever Occurring in Subjects Sensitive to Ragweed Pollen," Journal of Allergy 21(4):282-287.

Carter, P. et al. (Feb. 1992). "High Level *Escherichia coli* Expression and Production of a Bivalent Humanized Antibody Fragment," BioTechnology 10:163-167.

Case, M. E. et al. (Oct. 1979)."Efficient Transformation of Neurospora Crassa by Utilizing Hybrid Plasmid DNA," Proc. Natl. Acad. Sci. U. S. A. 76(10):5259-5263.

Cella, M. et al. (Feb. 2009, e-pub. Nov. 2, 2008). "A Human Natural Killer Cell Subset Provides an Innate Source of IL-22 for Mucosal Immunity," Nature 457:722-725, 11 pages.

Chan, H.L-Y. et al. (Jun. 2007). "How Should We Manage Patients With Non-Alcoholic Fatty Liver Disease In 2007?" Journal of Gastroenterology and Hepatology 22(6):801-808.

Chang, A.C.Y. et al. (Oct. 19, 1978). "Phenotypic Expression in *E. coli* of a DNA Sequence Coding for Mouse Dihydrofolate Reductase," Nature 275(5681):617-624.

Cheadle, C. et al. (Jan. 1992). "Cloning and Expression of the Variable Regions of Mouse Myeloma Protein MOPC315 in *E. coli*: Recovery of Active FV Fragments," Mol Immunol 29(1):21-30.

Choi, S. M. et al. (Mar. 2013). "Innate Stat3—Mediated Induction of the Antimicrobial Protein Reg3γ is Required for Host Defense Against MRSA Pneumonia," J. Exp. Med. 210(3):551-561.

Clayburgh, D.R. et al. (Mar. 2004; e-published on Jan. 19, 2004). "A Porous Defense: the Leaky Epithelial Barrier in Intestinal Disease," Lab. Invest. 84(3):282-291.

Clinical Research (2006). vol. 83, No. 2, p. 238-242. (Cited in the Japanese Decision of Refusal dated Aug. 29, 2013 for Japanese Patent Application No. 2010-520208), ten pages. (Partial English Translation).

Clynes, R. et al. (Jan. 20, 1998). "Fc Receptors Are Required in Passive and Active Immunity to Melanoma," Proc. Nat'l Acad. Sci. USA 95(2):652-656.

Cobleigh, M.A. et al. (Jan. 2013). "Protective and Pathological Properties of IL-22 in Liver Disease: Implications for Viral Hepatitis," Am. J. Pathology 182(1):21-28.

Couturier, M. et al. (Jul. 2013, e-pub Feb. 12, 2013). "IL-22 Deficiency in Donor T Cells Attenuates Murine Acute Graft-Versus-Host Disease Mortality While Sparing The Graft-Versus-Leukemia Effect," *Leukemia*. 27(7):1527-1537.

Cox, G.N. et al. (2004). "Enhanced Circulating Half-Life and Hematopoietic Properties of a Human Granulocyte Colony-Stimulating Factor/Immunoglobulin Fusion Protein," Exp. Hematol. 32:441-449.

Cragg, M.S. et al. (Apr. 1, 2004). "Antibody Specificity Controls in Vivo Effector Mechanisms of anti-CD20 Reagents," Blood 103:2738-2743.

Cragg, M.S. et al. (Feb. 1, 2003). "Complement-mediated Lysis by anti-CD20 mAb Correlates With Segregation Into Lipid Rafts," Blood 101(3):1045-1052.

Craig, D.G.N. et al. (Feb. 2010, e-pub Oct. 21, 2009). "Review Article: The Current Management of Acute Liver Failure," Alimentary Pharmacology and Therapeutics 31(3):345-358.

Dall'Acqua, W. et al. (Jun. 30, 1998). "Contribution of Domain Interface Residues to the Stability of Antibody CH3 Domain Homodimers," Biochem. 37(26):9266-9273.

Dambacher, J. et al. (Mar. 2008). "The Role of Interleukin-22 in Hepatitis C Virus Infection," Cytokine 41(3):209-216.

Das, R. et al. (Mar. 5, 2009). "Interleukin-23 Secretion by Donor Antigen-Presenting Cells is Critical for Organ-Specific Pathology in Graft-Versus-Host Disease," Blood 113(10):2352-2362.

De Boer, H.A. et al. (Jan. 1983). "The tac Promoter: A Functional Hybrid Derived from the trp and lac Promotors," Proc. Natl. Acad. Sci. USA 80:21-25.

De Lau, W. et al. (Aug. 18, 2011). "Lgr5 Homologues Associate with Wnt Receptors and Mediate R-spondin Signalling," *Nature* 476:293-297.

De Oliveira Neto, M. et al. (Mar. 1, 2008; e-pub. Nov. 16, 2007). "Interleukin-22 Forms Dimers That are Recognized by Two Interleukin-22R1 Receptor Chains," *Biophys. J.* 94(5):1754-1765.

Delaney, A.P. et al. (2011). "The Role of Albumin as a Resuscitation Fluid For Patients With Sepsis: A Systematic Review and Meta-Analysis," Grit Care Med 39(2):386-391.

Diefenbach, A. (Aug. 24, 2012). "Interleukin-22, the Guardian of the Intestinal Stem Cell Niche?" Immunity 37:196-198.

Dimartino, J.F. et al. (Sep. 1999). "Mll Rearrangements in Haematological Malignancies: Lessons from Clinical and Biological Studies," Br J Haematol. 106(3):614-626.

Dubois, M.-J. et al. (Oct. 2006). "Albumin Administration Improves Organ Function in Critically Ill Hypoalbuminemic Patients: A Prospective, Randomized, Controlled, Pilot Study," Grit Care Med 34(10)2536-2540 (Abstract Only).

(56) References Cited

OTHER PUBLICATIONS

Dudakov, J.A. et al. (Apr. 6, 2012; Epub Mar. 1, 2012) "Interleukin-22 drives endogenous thymic regeneration in mice," Science. 336(6077):91-95.
Dudakov, J.A. et al. (Epub Feb. 11, 2015) "Interleukin-22: immunobiology and pathology," Annu Rev Immunol. 33:747-85.
Dumoutier, L. et al. (Aug. 29, 2000). "Human Interleukin-10-Related T Cell-Derived Inducible Factor: Molecular Cloning and Functional Characterization as an Hepatocyte-Stimulating Factor," PNAS 97(18):10144-10149.
Dumoutier, L. et al. (Feb. 15, 2000). "Cloning and Characterization of IL-10-Related T Cell-Derived Inducible Factor (IL-TIF), a Novel Cytokine Structurally Related to IL-10 and Inducible by IL-9," The Journal of Immunology 164(4):1814-1819.
Duncan, A.R. et al. (Apr. 21, 1988). "The Binding Site for C1q on IgG," Nature 332(6166):738-740.
EBI Accession No. AWL86673. (May 26, 2018). "Streptomyces Globisporus Elongation Factor Tu," Located at URL: <https://www.ebi.ac.uk/ena/data/view/AWL86673&display=text>, last visited on May 31, 2018, 2 pages.
Eriguchi, Y. et al. (Jul. 5, 2012, e-pub. Apr. 24, 2012). "Graft-Versus-Host Disease Disrupts Intestinal Microbial Ecology by Inhibiting Paneth Cell Production of α-Defensins," *Blood* 120(1):223-231.
Eyerich, S. et al. (Sep. 2010; e-pub. Aug. 4, 2010). "IL-17 and IL-22: Siblings, Not Twins," Trends Immunol. 31(9):354-361.
Feng, D. et al. (2012, e-pub. Jan. 1, 2012). "Interleukin-22 Ameliorates Cerulein-Induced Pancreatitis in Mice by Inhibiting the Autophagic Pathway," International Journal of Biological Sciences 8(2):249-257.
Ferrara, J. L. (Oct. 1993). "Cytokine Dysregulation as a Mechanism of Graft Versus Host Disease," Curr Opin Immunol. 5(5):794-799.
Ferrara, J. L., et al. (May 2, 2009). "Graft-Versus-Host Disease," Lancet 373:1550-1561, 25 pages.
Fleer, R. et al. (Oct. 1, 1991). "Stable Multicopy Vectors for High-Level Secretion of Recombinant Human Serum Albumin by Kluyveromyces Yeasts," Bio/Technology 9(10):968-975.
Food and Drug Administration. (Jul. 2005). "Guidance For Industry: Estimating the Maximum Safe Starting Dose in Initial Clinical Trials For Therapeutics in Adult Healthy Volunteers," Center For Drug Evaluation and Research (CDER) 7(0.001):30 pages.
Food and Drug Administration. (May 5, 2016). "Drug Research and Children," 2 pages, as retrieved on Feb. 7, 2022 from https://www.fda.gov/drugs/information-consumers-and-patients-drugs/drug-research-and-children.
Gan, M. et al. (2006). "The Progress of Multiple Organ Dysfunction Syndrome," Medical Recapitulate 14:14. (Abstract Only).
Gao, B. (Apr. 2005). "Cytokines, STATs and Liver Disease," Cell. Mol. Immunol. 2(2):92-100.
Gao, B. et al. (Jul. 2019, e-pub Jun. 19, 2018). "Interleukin-22 From Bench to Bedside: A Promising Drug For Epithelial Repair," Cellular & Molecular Immunology 16(7):666-667.
Gao, H. et al. (Jun. 2006, e-pub. Apr. 20, 2006). "Long-Term Administration of Estradiol Decreases Expression of Hepatic Lipogenic Genes and Improves Insulin Sensitivity in ob/ob Mice: A Possible Mechanism is through Direct Regulation of Signal Transducer and Activator of Transcription 3," Molecular Endocrinology 20(6):1287-1299.
Gavrieli, Y. et al. (Nov. 1992) "Identification of programmed cell death in situ via specific labeling of nuclear DNA fragmentation." J Cell Biol. 119:493-501.
Gazzano-Santoro, H. et al. (Mar. 28, 1997). "A Non-Radioactive Complement-Dependent Cytotoxicity Assay for anti-CD20 Monoclonal Antibody," J. Immunol. Methods 202(2):163-171.
Generon BioMed Holding Ltd. (Nov. 13, 2018). "Generon's F-652 Shows Positive Results in An Open Label, Cohort Dose Escalation Study to Assess the Safety and Efficacy in Patients with Alcoholic Hepatitis", located at https://www.businesswire.com/news/home/20181113005520/en/Generon%E2%80%99s-F-652-Shows-Positive-Results-%E2%80%9CAn-Open, last visited on Mar. 20, 2020, 2 pages.
Gerbitz, A. et al. (Jun. 1, 2004, e-pub. Feb. 12, 2004). "Probiotic Effects on Experimental Graft-Versus-Host Disease: Let Them Eat Yogurt," Blood 103(11):4365-4367.
Gething, M.J. et al. (Oct. 22, 1981). "Cell-Surface Expression of Influenza Haemagglutinin from a Cloned DNA the RNA Gene," Nature, 293:620-625.
Gill, H.K. et al. (Jan. 21, 2006). "Non-Alcoholic Fatty Liver Disease and the Metabolic Syndrome: Effects of Weight Loss and a Review of Popular Diets. Are Low Carbohydrate Diets the Answer?" World Journal of Gastroenterology 12(3):345-353.
Glinka, A. et al. (Sep. 30, 2011, e-pub. Sep. 9, 2011). "LGR4 and LGR5 are R-spondin Receptors Mediating Wnt/β-Catenin and Wnt/PCP Signalling," EMBO Rep. 12(10):1055-1061.
Goeddel, D.V. et al. (Oct. 18, 1979). "Direct Expression in *Escherichia coli* of a DNA Sequence Coding For Human Growth Hormone," Nature 281:544-548.
Goeddel, D.V. et al. (Sep. 25, 1980). "Synthesis of Human Fibroblast Interferon by *E. coli*l," Nucleic Acids Res. 8(18):4057-4074.
Good, M. et al. (May 1, 2015). "The Role of IL-22 Signaling in the Pathogenesis of Necrotizing Enterocolitis (HUM1P.314)," The Journal of Immunology 194(Supplement 1): Abstract No. 52.39, 4 pages.
Graham, F.L. et al. (1977). "Characteristics of a Human Cell Line Transformed by DNA from Human Adenovirus Type 5," J. Gen Virol, 36:59-72.
Graham, F.L. et al. (Apr. 1973). "A New Technique for the Assay of Infectivity of Human Adenovirus 5 DNA," Virology 52(2):456-467.
Grattagliano, I. et al. (May 2007). "Managing Nonalcoholic Fatty Liver Disease: Recommendations for Family Physicians," Canadian Family Physician 53(5):857-863.
Greenwald, R.B. et al. (Oct. 20, 1994). "Highly Water Soluble Taxol Derivatives: 2'-Polyethyleneglycol Esters as Potential Prodrugs," Bioorg. Med. Chem. Lett. 4(20):2465-2470.
Guss, B. et al. (Jul. 1986). "Structure of the IgG-Binding Regions of Streptococcal Protein G," EMBO J. 5(7):1567-1575.
Guyer, R.L. et al. (Aug. 1976). "Immunoglobulin Binding by Mouse Intestinal Epithelial Cell Receptors," J. Immunol. 117(2):587-593.
Hale, L.P. et al. (Mar. 10, 2008). "Treatment of Experimental Colitis in Mice With LMP-420, an Inhibitor of TNF Transcription," *J Inflamm (Land)*. 5(4): 13 pages.
Hanash, A. et al. (Feb. 2012). "Host-Derived IL-22 Protects Intestinal Stem Cells from GvHD," Biology of Blood and Marrow Transplantation 18(2): Abstract No. 426, S361-S362.
Hanash, A.M. (Aug. 26, 2012). "IL-22 In Epithelial Regeneration After Allogeneic Transplant," NIH Report Portfolio Online Reporting Tools, 5 pages. (Abstract Only).
Hanash, A.M. et al. (2012). "Effect of IL-22 on Intestinal Stem Cells, GVHD-related Tissue Damage, and GVL," Journal of Clinical Oncology: 6539, 1 page. (Abstract Only).
Hanash, A.M et al. (Aug. 24, 2012). "Interleukin-22 Protects Intestinal Stem Cells from Immune-mediated Tissue Damage and Regulates Sensitivity to Graft Versus Host Disease," *Immunity* 37(2):339-350.
Hanash, A.M. et al. (Nov. 18, 2011). "Host-Derived IL-22 Limits Graft Versus Host Disease and Protects the Intestinal Stem Cell Niche," *Blood*. 118(21):309, 7 pages. (Abstract Only).
Heel, K. A. et al. (Feb. 1997). "Review: Peyer's Patches," Journal of Gastroenterology and Hepatology 12(2):122-136.
Heida, F. H. et al. (Aug. 2016, e-pub. Apr. 6, 2016). "Paneth Cells in the Developing Gut: When Do They Arise and When are They Immune Competent?" Pediatric Research 80(2):306-310.
Hellstrom, I. et al. (Mar. 1985). "Strong Antitumor Activities of IgG3 Antibodies to a Human Melanoma-Associated Ganglioside," Proc. Nat'l Acad. Sci. USA 82(5):1499-1502.
Hellstrom, I. et al. (Sep. 1986). "Antitumor Effects of L6, an IgG2a Antibody That Reacts With Most Human Carcinomas," Proc. Nat'l Acad. Sci. USA 83(18):7059-7063.
Henikoff, S. et al. (Nov. 15, 1992). "Amino Acid Substitution Matrices From Protein Blocks," Proc. Nat'l Acad. Sci. USA 89:10915-10919.

(56) References Cited

OTHER PUBLICATIONS

Herrine, S.K. et al. (Jan. 2018). "Fatty Liver Hepatic Steatosis," Merck Manual, one page only.
Hess, B. et al. (1969). "Cooperation of Glycolytic Enzymes," Adv Enzyme Regul. 7:149-167.
Hill, G.R. et al. (May 1, 2000). "The Primacy of the Gastrointestinal Tract as a Target Organ of Acute Graft-Versus-Host Disease: Rationale for the use of Cytokine Shields in Allogeneic Bone Marrow Transplantation," Blood 95(9):2754-2759.
Hines, I.N. et al. (Aug. 2004). "Recent Advances in Alcoholic Liver Disease III. Role of the Innate Immune Response in Alcoholic Hepatitis," American Journal of Physiology—Gastrointestinal and Liver Physiology 287(2):G310-G314.
Hitzeman, R.A. et al. (Dec. 25, 1980). "Isolation and Characterization of the Yeast 3-Phosphoglycerokinase Gene (PKG) by an Immunological Screening Technique," J. Biol. Chem. 255(24):12073-12080.
Holland, J.P. (Nov. 14, 1978). "Isolation and Identification of Yeast Messenger Ribonucleic Acids Coding For Enolase, Glyceraldehyde-3-Phosphate Dehydrogenase, and Phosphoglycerate Kinase," Biochemistry 17(23):4900-4907.
Hong, F. et al. (Oct. 2004). "Interleukin 6 Alleviates Hepatic Steatosis and Ischemia/Reperfusion Injury in Mice with Fatty Liver Disease," Hepatology 40(4):933-941.
Hsiao, C.L. et al. (Aug. 1979). "High-Frequency Transformation of Yeast by Plasmids Containing the Cloned Yeast ARG4 Gene," Proc. Natl. Acad. Sci. (USA) 76(8):3829-3833.
Hua, G. et al. (Nov. 2012, e-pub. Jul. 27, 2012). "Crypt Base Columnar Stem Cells in Small Intestines of Mice are Radioresistant," Gastroenterology 143:1266-1276, 18 pages.
Huber, S. et al. (Nov. 8, 2012, Epub Oct. 17, 2012) "IL-22BP is regulated by the inflammasome and modulates tumorigenesis in the intestine." Nature, 491(7423):259-263.
Hwang, T.-L. (May 2009). "Potential Use of Albumin Administration in Severe Sepsis," J Chin Med Assoc 72(5):225-226.
Idusogie, E.E. et al. (Apr. 15, 2000). "Mapping of the C1q Binding Site on Rituxan, a Chimeric Antibody With a Human IgG1 Fc," J. Immunol. 164(8):4178-4184.
Inoue, H. et al. (Feb. 2004; e-published on Jan. 11, 2004). "Role of STAT-3 in Regulation of Hepatic Gluconeogenic Genes and Carbohydrate Metabolism In Vivo," Nat Med. 10(2):168-174, (English Abstract only).
International Diabetes Federation. (2006). "The IDF Consensus Worldwide Definition of the Metabolic Syndrome," 24 pages.
International Preliminary Examination Report Completed on Sep. 3, 2009 for International Application No. PCT/US2008/071859 filed on Aug. 1, 2008, four pages.
International Preliminary Report on Patentability dated Jul. 10, 2014, for International Application No. PCT/CN2012/087694, filed Dec. 27, 2012, 21 pages (with attached English translation of the Written Opinion of the International Searching Authority).
International Preliminary Report on Patentability dated Jul. 10, 2007, for International Application No. PCT/US05/28186, filed Aug. 8, 2005, four pages.
International Preliminary Report on Patentability dated Jul. 21, 2011, for International Application No. PCT/US2010/20673, filed Jan. 11, 2010, six pages.
International Preliminary Report on Patentability dated Mar. 14, 2013, for International Application No. PCT/CN2011/079124, filed Aug. 30, 2011, fourteen pages (with attached English translation).
International Preliminary Report on Patentability dated May 10, 2016 for International Application No. PCT/CN2014/090520, filed on Nov. 6, 2014, six pages.
International Preliminary Report on Patentability dated May 10, 2016 for International Application No. PCT/US2014/064655, filed on Nov. 7, 2014, eleven pages.
International Preliminary Report on Patentability dated May 19, 2016, for International Application No. PCT/CN2014/090519, filed Nov. 6, 2014, seven pages.
International Preliminary Report on Patentability dated Oct. 25, 2018 for International Application No. PCT/US2017/027806 filed on Apr. 14, 2017, seven pages.
International Search Report and Written Opinion dated Jun. 23, 2017 for International Application No. PCT/US2017/027806, filed on Apr. 14, 2017, twelve pages.
International Search Report and Written Opinion dated Mar. 27, 2015 for International Application No. PCT/US2014/064655, filed on Nov. 7, 2014, sixteen pages.
International Search Report dated Mar. 9, 2010, for International Application No. PCT/US10/20673, filed Jan. 11, 2010, three pages.
International Search Report dated May 3, 2006, for International Application No. PCT/US05/28186, filed Aug. 8, 2005, one page.
International Search Report dated Nov. 26, 2008, for International Application No. PCT/US08/71859, filed Aug. 1, 2008, one page.
International Search Report dated Apr. 18, 2013, for International Application No. PCT/CN2012/087694, filed on Dec. 27, 2012, four pages.
International Search Report dated Dec. 8, 2011 for International Application No. PCT/CN2011/079124, filed on Aug. 30, 2011, four pages.
International Search Report dated Feb. 10, 2015 for International Application No. PCT/CN2014/090520 filed on Nov. 6, 2014, five pages.
International Search Report dated Jan. 30, 2015 for International Application No. PCT/CN2014/090519 filed Nov. 6, 2014, six pages.
Ivanov, S. et al. (Jun. 30, 2013). "Interleukin-22 Reduces Lung Inflammation During Influenza A Virus Infection and Protects Against Secondary Bacterial Infection and Protects Against Secondary Bacterial Infection," Journal of Virology 12(87)6911-6924.
Jenq, R.R. et al. (Mar. 2010; e-published on Feb. 19, 2010). "Allogeneic Haematopoietic Stem Cell Transplantation: Individualized Stem Cell and Immune Therapy of Cancer," Nat Rev Cancer 10(3)213-220; pp. 1-10 (advance publication).
Jenq, R.R. et al. (May 2012, e-pub. Apr. 30, 2012). "Regulation of Intestinal Inflammation by Microbiota Following Allogeneic Bone Marrow Transplantation," The Journal of Experimental Medicine 209(5):903-911.
Jiang, R. et al. (Dec. 2013). "IL-22 is Related to Development of Human Colon Cancer By Activation of STAT3," BMC Cancer 13(1):59.
Jiang, R. et al. (Sep. 2, 2011). "Interleukin-22 Promotes Human Hepatocellular Carcinoma by Activation of STAT3," Hepatology 54(3):900-909.
Johnson, O.L. et al. (Jul. 1996). "A Month-Long Effect from a Single Injection of Microencapsulated Human Growth Hormone," Nature Medicine 2(7):795-799.
Jones, B.C et al. (Apr. 1, 2008; e-pub. Mar. 21, 2008). "Crystallization and Preliminary X-Ray Diffraction Analysis of Human IL-22 Bound to the Extracellular IL-22R1 Chain," Acta Crystall. Sect. F. Structure Biol. Cryst. Commun. F64(Pt. 4):266-269.
Jones, E.W. (Jan. 1977). "Proteinase Mutants of Saccharomyces Cerevisiae," Genetics 85(1):23-33.
Kappel, L.W. et al. (Jan. 22, 2009, e-pub. Oct. 17, 2008). "IL-17 Contributes to CD4-Mediated Graft-Versus-Host Disease," Blood 113(4):945-952.
Kelly, J.M. et al. (Feb. 1985). "Transformation of Aspergillus Niger by the amdS Gene of Aspergillus Nidulans," EMBO J. 4(2):475-479.
Keown, W.A. et al. (1990). "Methods for Introducing DNA into Mammalian Cells," Methods in Enzymology 185:527-537.
Ki, S.H. et al. (Oct. 2010). "Interleukin-22 Treatment Ameliorates Alcoholic Liver Injury in a Murine Model of Chronic-Binge Ethanol Feeding: Role of Signal Transducer and Activator of Transcription 3," Hepatology 52(4):1291-1300.
Killen, J.A. et al. (Nov. 1, 1984). "Specific Killing of Lymphocytes That Cause Experimental Autoimmune Myasthenia Gravis By Ricin Toxin-Acetylcholine Receptor Conjugates," J. Immunol. 133(5):2549-2553.
Kim, T.W. et al. (Jan. 14, 2006). "Involvement of Lymphocytes in Dextran Sulfate Sodium-Induced Experimental Colitis," World J Gastroenterol. 12(2):302-305.

(56) References Cited

OTHER PUBLICATIONS

Kingsman, A.J. et al. (Oct. 1979). "Replication in *Saccharomyces cerevisiae* of Plasmid pBR313 Carrying DNA from the Yeast trpl Region," Gene 7(2): 141-152.

Klöppel, G. et al. (1991). "Chronic Pancreatitis: Evolution of the Disease," Hepato-gastroenterology 38(5):408-412.

Knaus, W.A. et al. (Dec. 1985) "Prognosis in Acute Organ-System Failure," Ann. Surg. 202(6):685-693.

Kolls, J. K., et al., (Nov. 2008). "Cytokine-Mediated Regulation of Antimicrobial Proteins," Nat Rev Immunol, 8(11):829-835, 14 pages.

Kotenko, S.V. et al. (Sep. 8, 1995). "Interaction Between the Components of the Interferon γ Receptor Complex," J. Biol. Chem. 270(36):20915-20921.

Kreymborg, K. et al. (Dec. 2007). "IL-22 is Expressed by Th17 Cells in an IL-23—Dependent Fashion, but Not Required for the Development of Autoimmune Encephalomyelitis," J Immunol 179:8098-8104.

Krijanovski, O.I. et al. (Jul. 15, 1999). "Keratinocyte Growth Factor Separates Graft-Versus-Leukemia Effects From Graft-Versus-Host Disease," Blood 94(2): 825-831.

Krivtsov, A.V. et al. (Aug. 2006, e-pub. Jul. 16, 2006). "Transformation from Committed Progenitor to Leukaemia Stem Cell Initiated by MLL-AF9," Nature. 442(7104):818-822.

Kuroiwa, T. et al. (Jun. 2001). "Hepatocyte Growth Factor Ameliorates Acute Graft-Versus-Host Disease and Promotes Hematopoietic Function," J. Clin. Invest 107:1365-1373.

Lamarthee at al. (2016), Interleukin-22 in Graft-Versus-Host Disease after Allogeneic Stem Cell Transplantation, Front. Immunol. 7:148.

Lee, W.-C. at al. (Jan. 2010). "Palmatine Attenuates D-Galactosamine/Lipopolysaccharide-Induced Fulminant Hepatic Failure in Mice," Food Chem Toxicol 48(1):222-228.

Lei, K. et al. (May 19, 1995). "Structure-Function Analysis of Human Glucose-6-Phosphatase, the Enzyme Deficient in Glycogen Storage Disease Type 1a," The Journal of Biological Chemistry 270(20):11882-11886.

Levine, J.E. et al. (Aug. 22, 2013, e-pub. Jun. 12, 2013). "Low Paneth Cell Numbers at Onset of Gastrointestinal Graft-Versus-Host Disease Identify Patients at High Risk for Nonrelapse Mortality," Blood 122(8):1505-1509.

Lewis, D.H. (1990). "Controlled Release of Bioactive Agents From Lactide/Glycolide Polymer," in Chapter 1 of Biodegradable Polymers as Drug Delivery Systems, Chasin, M. (ed.) et al., Marcel Dekker Inc. New York, 1990, pp. 1-41, fifty two pages.

Li, H. et al. (2016). "Gastrointestinal Stem Cells in Health and Disease: From Flies to Humans," Dis Model Mech 9: 487-499.

Li, Q. (Sep. 2003). "Research Development of Interleukin-22," Chinese J. of Cancer Biotherapy 10(3):226-228 (Translation of Abstract Only).

Lieber, C.S. et al. (Mar. 1966). "Study of Agents for the Prevention of the Fatty Liver Produced by Prolonged Alcohol Intake," Gastroenterology 50(3):316-322.

Lieber, C.S. et al. (Oct. 1989). "Experimental Methods of Ethanol Administration," Hepatology 10(4):501-510.

Lindemans, C. et al. (2014). "IL-22 Administration Protects Intestinal Stem Cells from Gvhd," Biol Blood Marrow Transplant 20(2): Supp. SUPPL. 1, Abstract No. 49:553-554.

Lindmark, R. et al. (Aug. 12, 1983). "Binding of Immunoglobulins to Protein A and Immunoglobulin Levels in Mammalian Sera," J. Immunol. Meth. 62(1):1-13.

Louvencourt, L.D. et al. (May 1983). "Transformation of Kluyveromyces Lactis by Killer Plasmid DNA," J. Bacterial. 154(2):737-742.

Low, S.C. et al. (Jul. 2005). "Oral and Pulmonary Delivery of FSH-Fc Fusion Proteins Via Neonatal Fc Receptor-Mediated Transcytosis," Human Reproduction 20(7):1805-1813.

Ma, H.L. (Feb. 2008). "IL-22 is Required For Th17 Cell-Mediated Pathology in a Mouse Model of Psoriasis-Like Skin Inflammation," J Clin Invest. 118(2):597-607.

Mansour, S.L. et al. (Nov. 24, 1988). "Disruption of the Proto-Oncogene Int-2 in Mouse Embryo-Derived Stem Cells: A General Strategy for Targeting Mutations to Non-Selectable Genes," Nature 336:348-352.

Mantei, N. et al. (Sep. 6, 1979). "Rabbit β-globin mRNA Production in Mouse L Cells Transformed with Cloned Rabbit β-Globin Chromosomal DNA," Nature 281:40-46.

Marchesini, G. et al. (Aug. 2001). "Nonalcoholic Fatty Liver Disease. A Feature of the Metabolic Syndrome," Diabetes 50(8):1844-1850.

Mather, J.P. (Aug. 1980) "Establishment and Characterization of Two Distinct Mouse Testicular Epithelial Cell Lines, " Biol. Reprod. 23(1):243-252.

Matsusue, K. et al. (Mar. 2003). "Liver-Specific Disruption of Ppary in Lepiin-Deficient Mice Improves Fatty Liver But Aggravates Diabetic Phenotyps," J. Clin. Invest. 111 (5):737-747.

Matthews, J. R. et al. (Dec. 2011). "Absolute Requirement for STAT3 Function in Small-Intestine Crypt Stem Cell Survival," Cell Death Differ 18:1934-1943.

Mavrelis, P.G. et al. (1983). "Hepatic Free Fatty Acids in Alcoholic Liver Disease and Morbid Obesity," Hepatology 3(2):226-231.

Max Bayard, M.D. et al. (Jun. 1, 2006). "Nonalcoholic Fatty Liver Disease," American Family Physician 73(11):1961-1968.

McGee, H. M. et al. (2013, e-pub. Dec. 06, 2012). "IL-22 Promotes Fibroblast-Mediated Wound Repair in the Skin," Journal of Investigative Dermatology 133(5):1321-1329.

Medema, J.P. et al. (Jun. 16, 2011). "Microenvironmental Regulation of Stem Cells in Intestinal Homeostasis and Cancer," Nature 474:318-326.

Mertelsmann, A.M. et al. (2013). "IL-22 Administration Decreases Intestinal Gvhd Pathology, Increases Intestinal Stem Cell Recovery, and Enhances Immune Reconstruction Following Allogeneic Hematopietic Transplantation," Blood 122(22), Abstract 290, 3 pages.

Mitra, A. et al. (2012). "Functional Role of IL-22 in Psoriatic Arthritis," Arthritis Research & Therapy 14(2):1-10.

Mordenti, J. et al. (1989). "The Use of Interspecies Scaling in Toxicokinetics," Chapter 4 in Toxicokinetics and New Drug Development, Yacobi A. ed. et al.; Pergamon Press, New York, pp. 42-96.

Morris, H.G. (Jan. 1985). "Mechanisms of Action and Therapeutic Role of Corticosteroids in Asthma," Allergy Clin. Immunol. 75(1 Pt 1):1-13.

Mortele, K.J. et al. (Nov. 2004). "A Modified CT Severity Index for Evaluating Acute Pancreatitis: Improved Correlation With Patient Outcome," American Journal of Roentgenology 183:1261-1265.

Muhl, H. et al. (Jun. 2013). "IL-22 in Tissue-Protective Therapy," Br. J. Pharmacol. 169(4):761-771.

Nagalakshmi, M.L. et al. (May 2004). "Interleukin-22 Activates STAT3 and Induces IL-10 by Colon Epithelial Cells," International Immunopharmacology 4(5):679-691.

NIH (Feb. 11, 2009). "Antibiotics for the Treatment of Ulcerative Colitis," ClinicalTrials.gov, No. NCT00355602, 8 pages, retrieved from https://clinicaltrials.gov/ct2/show/NCT00355602.

NIH (Jan. 14, 2016). "Use of F-652 in Patients With Alcoholic Hepatitis (TREAT 008)," ClinicalTrials.gov, No. NCT02655510, 8 pages, retrieved from https://clinicaltrials.gov/ct2/show/.

NIH (Jun. 30, 2018). "RePORTER Frequently Asked Questions (FAQ)," NIH Research Portfolio Online Reporting Tools (RePORT), 2 pages.

Nilson, B.H.K. at al. (Feb. 5, 1992). "Protein L From Peptostreptococcus Magnus Binds to the Kappa Light Chain Variable Domain," J. Biol. Chem. 267(4):2234-2239.

Nursing and Midwifery Council (Nov. 19, 2007). "The Administration of Medicines," Medicines Management, 7 pages.

Oki, K. et al. (2016, e-pub. Nov. 28, 2016). "Comprehensive Analysis of the Fecal Microbiota of Healthy Japanese Adults Reveals a New Bacterial Lineage Associated With a Phenotype Characterized By A High Frequency of Bowel Movements and a Lean Body Type," BMC Microbiology 16:284, 13 pages.

Pan, H. et al. (Feb. 2004). "Hydrodynamic Gene Delivery of Interleukin-22 Protects the Mouse Liver from Concanavalin A-, Carbon Tetrachloride-, and Fas Ligand-Induced Injury Via Activation of STAT3," Cell. Mol. Immunol. 1(1):43-49.

(56) References Cited

OTHER PUBLICATIONS

Papathanassoglou, E.D.E. et al. (Sep. 2008). "Multiple Organ Dysfunction Syndrome Pathogenesis and Care: A Complex Systems' Theory Perspective," Nursing in Critical Care 13(5):249-259. (Abstract Only).
Parks, O.B. et al. (Jan. 13, 2016). "Interleukin-22 Signaling in the Regulation of Intestinal Health and Disease," Frontiers in Cell and Developmental Biology 3:1-13(Article 85).
Pearson, C. et al. (Jun. 2012; e-published on May 10, 2012). "Lymphoid Microenvironments and Innate Lymphoid Cells in the Gut," Trends Immunol 33(6):289-296.
Peery, A. F. et al. (Nov. 2012, e-pub. Aug. 8, 2012). "Burden of Gastrointestinal Disease in the United States-2012 Update," Gastroenterology 143(5):1179-1187, 19 pages.
Petkova, S.B. et al. (Dec. 2006, e-pub. Oct. 31, 2006). "Enhanced Half-Life of Genetically Engineered Human lgG1 Antibodies in a Humanized FcRn Mouse Model: Potential Application in Humorally Mediated Autoimmune Disease," Int'l. Immunol. 18(12):1759-1769.
Petrovic, A. et al. (Feb. 15, 2004; Epub Oct. 16, 2003) "LPAM (alpha 4 beta 7 integrin) is an important homing integrin on alloreactive T cells in the development of intestinal graft-versus-host disease." Blood. 103:1542-1547.
Piaggesi, A. et al. (Oct. 17-19, 2019). "A Randomized, Multiple-Dose Study of Subcutaneous UTTR1147A (IL-22Fc) in Patients with Neuropathic, Non-Healing Diabetic Foot Ulcers (DFUs)," Abstract IDL 67, Poster presented at Diabetic Foot Global Conference (DFCon), Oct. 17-19, 2019, Los Angeles, CA, 1 page.
Pickert, G. et al. (Jul. 2009, e-pub. Jun. 29, 2009). "STAT3 Links IL-22 Signaling in Intestinal Epithelial Cells to Mucosal Wound Healing," J. Exp. Med. 206(7):1465-1472.
Ponce, D.M. et al. (Jun. 2013). "Graft-versus-host Disease After Double-Unit Cord Blood Transplantation Has Unique Features and an Association with Engrafting Unit-Recipient HLA-match," Biol Blood Marrow Transplant 19(6): 904-911.
Qiu, Z. et al. (Jan. 2006). "Fibronectin Prevents D-Galactosamine/Lipopolysaccharide-Induced Lethal Hepatic Failure in Mice," Shock 25(1):80-87.
Quinlan, G.J. et al. (Oct. 1998). "Administration of Albumin to Patients With Sepsis Syndrome: A Possible Beneficial Role in Plasma Thiol Repletion," Clinical Science 95:459-465.
R&D System a bio-techne brand. Quantikine® ELISA Human IL-10 Immunoassay, Product Datasheets, located at: https://resources.mdsystems.com/pdfs/datasheets/d1000b.pdf, last visited on Mar. 20, 2020, 16 pages.
Raag, R. et al. (Jan. 1995). "Single-chain Fvs," FASEB 9(1):73-80.
Radaeva, S. et al. (May 2004). "Interleukin 22 (IL-22) Plays a Protective Role in T Cell-Mediated Murine Hepatitis: IL-22 is a Survival Factor for Hepatocytes Via STAT3 Activation," Hepatology 39(5): 1332-1342.
Rahman, T. M. (Apr. 2000). "Animal Models of Acute Hepatic Failure," International Journal of Experimental Pathology 81(2):145-157.
Ramakrishnan, S. et al. (Jan. 1984). "Comparison of the Selective Cytotoxic Effects of Immunotoxins Containing Ricin a Chain or Pokeweed Antiviral Protein and Anti-Thy 1.1 Monoclonal Antibodies," Cancer Res. 44:201-208.
Ramaswamy, S. et al. (2017). "Antinociceptive and Immunosuppressive Effect of Opioids in an Acute Postoperative SettingL An Evidence-Based Review," BJA Education 17(3):105-110.
Ravetch, J.V. et al. (1991). "Fc Receptors," Annu. Rev. Immunol. 9:457-492.
Reagan-Shaw, S. et al. (Oct. 17, 2007). "Dose Translation From Animal to Human Studies Revisited," The FASEB Journal 22(3):659-661.
Remick, D.G. et al. (May 2007). "Pathophysiology of Sepsis", Am J Pathol 170(5):1435-1444.
Rendon, J.L. et al. (Sep. 2012). "Th17 Cells: Critical Mediators of Host Responses to Burn Injury and Sepsis," Journal of Leukocyte Biology 92(3):529-538.
Res, P.C.M. et al. (Nov. 24, 2010). "Overrepresentation of IL-17A and IL-22 Producing CD8 T Cells in Lesional Skin Suggests Their Involvement in the Pathogenesis of Psoriasis," Plos One 5(11):e14108, 11 pages.
Richter, W.F, et al. (Sep. 2012). "Mechanistic Determinants of Biotherapeutics Absorption Following SC Administration," The AAPS Journal 14(3):559-570.
Riley, P. et al. (Dec. 2007; e-published on May 4, 2007). "A Growing Burden: The Pathogenesis, Investigation and Management of Non-Alcoholic Fatty Liver Disease," Journal of Clinical Pathology 60(12):1384-1391.
Roche (Dec. 2020). "Summary of Clinical Trial Results: A Study To Look at a New Medicine Called "UTTR1147A" —How Safe Are Different Doses For Healthy People and Patients To Take—and How is This Medicine Processed Through the Body," ClinicalTrialsGov no. NCT02749630, 10 pages.
Rothenberg, M. E. et al. (Jan. 2019). "Randomized Phase I Healthy Volunteer Study of UTTR 1147A (IL-22Fc): A Potential Therapy For Epithelial Injury," Clinical Pharmacology & Therapeutics 105(1):177-189.
Rutz, S. et al. (Dec. 2014). "The IL-20 Subfamily of Cytokines—From Host Defence to Tissue Homeostasis," Immunology 14:783-795.
Rutz, S. et al. (Feb. 13, 2013). "IL-22, Not Simply a Th17 Cytokine," Immunol Rev. 252(1):116-132, 1 page (Abstract Only).
Sale, G.E. (Mar. 1996). "Does Graft-Versus-Host Disease Attack Epithelial Stem Cells?," Mol Med Today 2(3): 114-119.
Sambrook, J. et al. (1989). Molecular Cloning—A Laboratory Manual, 2nd Edition, Maniatis, T.(ed.) et al., Cold Spring Harbor Laboratory Press, New York, NY pp. v-xxxii, twenty nine pages, (Table of Contents only).
Sanos, S. L. et al. (Mar. 2013, e-pub. Jan. 29, 2013) "Innate Lymphoid Cells: from Border Protection to the Initiation of Inflammatory Diseases," Immunol Cell Biol 91(3):215-224.
Sato, T. et al. (Jan. 20, 2011, e-pub. Nov. 28, 2010). "Paneth Cells Constitute the Niche for Lgr5 Stem Cells in Intestinal Crypts," Nature 469:415-418.
Sato, T. et al. (May 14, 2009; e-pub. Mar. 29, 2009). "Single Lgr5 Stem Cells Build Crypt-Villus Structures in Vitro without a Mesenchymal Niche," Nature 459:262-265.
Satoh-Takayama, N. et al. (Dec. 19, 2008). "Microbial Flora Drives Interleukin 22 Production in Intestinal NKp46+ Cells that Provide Innate Mucosal Immune Defense," Immunity 29(6):958-970.
Sawa, S. et al. (Apr. 2011, e-pub, Feb. 20, 2011). "RORγt+ Innate Lymphoid Cells Regulate Intestinal Homeostasis by Integrating Negative Signals from the Symbiotic Microbiota," Nat Immunol 12:320-326, thirty three pages.
Scheiermann, P. et al. (Apr. 2013). "Application of Interleukin-22 Mediates Protection in Experimental Acetaminophen-Induced Acute Liver Injury," The American Journal of Pathology 182(4):1107-1113.
Scheraga, H.A. (Jan. 1, 1992). "Predicting Three-Dimensional Structures of Oligopeptides," Lipkowitz, K., Boyd, D.B. (eds.) Reviews of Computational Chemistry, vol. 3, pp. 73-142. VCH Publ., New York.
Schmidt, J. et al. (Jan. 1992). "A Better Modal of Acute Pancreatitis for Evaluating Therapy," Annals of Surgery 215(1):44-56.
Schroeder, M. A., et al. (May 2011). "Mouse Models of Graft-Versus-Host Disease: Advances and Limitations," Dis Model Mech 4(3):318-333.
Sekikawa, A. et al. (Mar. 2010, e-pub. Jan. 11, 2010). "Involvement of the IL-22/REG Lα Axis in Ulcerative Colitis," Lab Invest 90(3):496-505.
Shaw, C.H. et.al. (Sep. 1983). "A General Method for the Transfer of Cloned Genes to Plant Cells," Gene 23(3):315-330.
Shields, R.L. et al. (Mar. 2, 2001, e-pub. Nov. 28, 2000). "High Resolution Mapping of the Binding Site on Human lgG1 for Fc Gamma Rl, Fc Gamma Rll, Fc Gamma Rlll, and FcRn and Design of lgG1 Variants With Improved Binding to the Fc Gamma R," J. Biol. Chem. 9(2):6591-6604.
Shin, J.-W. et al. (2010). "Interpretation of Animal Dose and Human Equivalent Dose for Drug Development," The Journal of Korean Oriental Medicine 31(3):1-7.

(56) References Cited

OTHER PUBLICATIONS

Shlomchik, E.D. (May 2007). "Graft-Versus-Host Disease," Nat. Rev. Immunol. 7(5):340-352.
Simons, B.D. et al. (Nov. 2011, e-pub. Jul. 20, 2011). "Stem Cell Self-Renewal in Intestinal Crypt," Exp Cell Res. 317(19):2719-2724.
Sonnenberg, G.F. et al. (Jan. 2011, e-pub. Dec. 30, 2010). "CD4(+) Lymphoid Tissue—Inducer Cells Promote Innate Immunity in the Gut," Immunity 34(1):122-134, 24 pages.
Sonnenberg, G.F. et al. (May 2011, e-pub. Apr. 19, 2011). "Border Patrol: Regulation of Immunity, Inflammation and Tissue Homeostasis at Barrier Surfaces by IL-22," Nat Immunol. 12(5):383-390.
Spits, H. et al. (Feb. 2013; e-published on Jan. 7, 2013). "Innate Lymphoid Cells—A Proposal for Uniform Nomenclature," Nat Rev Immunol 13:145-149, advance online publication pp. 1-5.
Sreekrishna, K. et al. (1988). "High Level Expression of Heterologous Proteins in Methylotrophic Yeast Pichia Pastoris," J. Basic Microbial. 28(4):265-278.
Stinchcomb, D.T. et al. (Nov. 1, 1979). "Isolation and Characterisation of a Yeast Chromosomal Replicator," Nature 282:39-43.
Stoner, K. L. et al. (2015, e-pub. Jul. 12, 2014). "Intravenous Versus Subcutaneous Drug Administration. Which Do Patients Prefer? A Systematic Review," The Patient-Patient-Centered Outcomes Research 8(2):145-153. (Abstract Only).
Stubbs, M.C. et al. (Jan. 2008, e-pub. Sep. 13, 2007). "MLL-AF9 and FLT3 Cooperation in Acute Myelogenous Leukemia: Development of a Model for Rapid Therapeutic Assessment," Leukemia 22:66-77, 21 pages.
Sugimoto, K. et al. (Feb. 2008). "IL-22 Ameliorates Intestinal Inflammation in a Mouse Model of Ulcerative Colitis," The Journal of Clinical Investigation 118(2): 534-544.
Takashima, S. et al. (Feb. 14, 2011, e-pub. Jan. 31, 2011). "The Wnt Agonist R-Spondin1 Regulates Systemic Graft—Versus-Host Disease by Protecting Intestinal Stem Cells," J Exp Med 208(2):285-294.
Takatsuka, H. et al. (2003). "Intestinal Graft-Versus-Host Disease: Mechanisms and Management," Drugs 63(1): 1-15. (Abstract Only).
Talbot, I. et al. (2006). "Graft-Versus-Host Disease," Biopsy Pathology in Colorectal Disease, 2Ed: Chapter 11.6, 192-194.
Tang, K.-Y et al. (2019, e-pub Apr. 18, 2018). "Safety, Pharmacokinetics, and Biomarkers of F-652, A Recombinant Human Interleukin-22 Dimer, In Healthy Subjects," Cellular & Molecular Immunology 16(5):473-482.
Tappe, D. et al. (2016, e-pub. Dec. 24, 2015). "Cytokine Kinetics of Zika Virus-Infected Patients From Acute to Reconvalescent Phase," Med Microbiol Immunol. 205:269-273.
Tilburn, J. et.al. (Dec. 1983). "Transformation by Integration in *Aspergillus nidulans*," Gene 26(2-3):205-221.
Tschemper, G. et al. (Jul. 1980). "Sequence of a Yeast DNA Fragment Containing a Chromosomal Replicator and the TRP1 Gene," Gene 10(2):157-166.
Tsunoda, S. et al. (May 1995). "Characterization of PEG-IL-6 and its Thrombopoetic Activity in Vivo," Drug Delivery System 10(3):175-180; (with English introduction).
Tymoczko, J.L. et al. (Dec. 23, 2011). "Membranes Define the Cell and Carry out Cellular Functions," Chapter 1.4 in Biochemistry a Short Course, Second Edition, W.H. Freeman and Company, New York, pp. 13-15, five pages.
U.S. Appl. No. 16/093,583, filed Oct. 12, 2018 by Kolls et al. (Copy not submitted herewith pursuant to the waiver of 37 C.F.R. § 1.98 (a)(2)(iii) issued by the Office on Sep. 21, 2004.).
U.S. Appl. No. 16/724,491, filed Dec. 23, 2019, by Marcel et al. (Copy not submitted herewith pursuant to the waiver of 37 C.F.R. § 1.98 (a)(2)(iii) issued by the Office on Sep. 21, 2004.).
Ueki, K. et al. (Jul. 13, 2004). "Central Role of Suppressors of Cytokine Signaling Proteins in Hepatic Steatosis, Insulin Resistance, and the Metabolic Syndrome in the Mouse," PNAS 101(28):10422-10427.

Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Van Den Berg, J.A. et al. (Feb. 1990). "Kluyveromyces as a Host For Heterologous Gene Expression: Expression and Secretion of Prochymosin," Bio/Technology 8(2):135-139.
Van Solingen, P. et al. (May 1977). "Fusion of Yeast Spheroplasts,"Journal of Bacteriology 130(2):946-947.
Varona, R. (Jul. 1, 2005, e-pub Mar. 17, 2005) "CCR6 Regulates CD4+ T-Cell-Mediated Acute Graft-Versus-Host Disease Responses," *Blood.* 106(1):18-26.
Velardi, E. et al. (Sep.-Oct. 2013; Epub Oct. 8, 2013) "Clinical strategies to enhance thymic recovery after allogeneic hematopoietic stem cell transplantation," Immunol Lett. 155(1-2):31-35.
Vitetta, E.S. et al. (Nov. 20, 1987). "Redesigning Nature's Poisons to Create Anti-Tumor Reagents," Science 238:1098-1104.
Wagner, F. et al. (2020). "P420 A Randomised, Observer-Blinded Phase 1b Multiple, Ascending Dose Study of UTTR1147A, An IL-22FC Fusion Protein, In Healthy Volunteers and Ulcerative Colitis Patients," Journal of Crohn's and Colitis 14(Supplement 1):S382-S383.
Walsh, M.C. et al. (Feb. 1986). "Necrotizing Enterocolitis: Treabnent Based on Staging Criteria", Pediatr Clin North Am. 33(1):179-201.
Wang, F. et al. (Aug. 2013, e-pub. May 2, 2013). "Isolation and Characterization of Intestinal Stem Cells Based on Surface Marker Combinations and Colony-Formation Assay," Gastroenterology 145:383-395, 18 pages.
Wang, X. et al. (Oct. 9, 2014). "Interleukin-22 Alleviates Metabolic Disorders Andrestores Mucosal Immunity in Diabetes," Nature 514(7521):237-241.
Weber, G.F. et al. (Apr. 2007, e-pub Jan. 29, 2007). "Inhibition of Interleukin-22 Attenuates Bacterial Load and Organ Failure During Acute Polymicrobial Sepsis," Infection and Immunity 75(4):1690-1697.
WHO. (Jul. 2015). "What is Hepatitis?" located at <http://www.who.int/features/qa/76/en/>, last visited on Jan. 15, 2016, three pages.
Wingard, J.R. et al. (Jun. 1, 2011). "Long-Term Survival and Late Deaths after Allogeneic Hematopoietic Cell Transplantation," J. Clin. Oncol. 29(16):2230-2239.
Witte, E. et al. (Oct. 2010, e-published on Sep. 25, 2010). "Interleukin-22: A Cytokine Produced by T, NK and NKT Cell Subsets, with Importance in the Innate Immune Defense and Tissue Protection," Cytokine Growth Factor Rev. 21(5):365-379.
Wolk, K. (Oct. 2006). "Interleukin-22: A Novel T- and NK-Cell Derived Cytokine That Regulates the Biology of Tissue Cells," Cytokine & Growth Factor Reviews 17(5):367-380. (Abstract Only).
Wolk, K. et al. (2009, e-pub Mar. 30, 2009). "IL-22 and IL-20 Are Key Mediators of the Epidermal Alterations in Psoriasis While IL-17 and IFN-γ Are Not," Journal of Molecular Medicine 87(5):523-536.
Wolk, K. et al. (Aug. 2004). "IL-22 Increases the Innate Immunity of Tissues," Immunity 21(2):241-254.
Wolk, K. et al. (Jun. 1, 2002). "Cutting Edge: Immune Cells as Sources and Targets of the IL-10 Family Members?," J. Immunology 168(11):5379-5402.
Wolk, K. et al. (May 2006). "IL-22 Regulates the Expression of Genes Responsible for Antimicrobial Defense, Cellular Differentiation, and Mobility in Keratinocytes: A Potential Role in Psoriasis," Eur J Immunol. 36:1309-1323.
Written Opinion of the International Searching Authority dated May 3, 2006, for International Application No. PCT/US05/28186, filed Aug. 8, 2005, three pages.
Written Opinion of the International Searching Authority dated Mar. 9, 2010, for International Application No. PCT/US10/20673, filed Jan. 11, 2010, four pages.
Written Opinion of the International Searching Authority dated Apr. 18, 2013 for International Application No. PCT/CN2012/087694, filed on Dec. 27, 2012, eleven pages.
Written Opinion of the International Searching Authority dated Dec. 8, 2011 for International Application No. PCT/CN2011/079124, filed on Aug. 30, 2011, seven pages.

(56) References Cited

OTHER PUBLICATIONS

Written Opinion of the International Searching Authority dated Feb. 10, 2015 for International Application No. PCT/CN2014/090520 filed on Nov. 6, 2014, four pages.
Written Opinion of the International Searching Authority dated Jan. 30, 2015 for International Application No. PCT/CN2014/090519 filed Nov. 6, 2014, five pages.
Written Opinion of the International Searching Authority dated Nov. 26, 2008 for International Application No. PCT/US2008/071859 filed on Aug. 1, 2008, five pages.
Wu, C. et al. (Nov. 2007; e-pub. Oct. 14, 2007). "Simultaneous Targeting of Multiple Disease Mediators by a Dual-Variable-Domain Immunoglobulin," *Nat. Biotechnol.* 25(11):1290-1297.
Xie, M.H. et al. (Oct. 6, 2000; e-pub. Jun. 29, 2000). "Interleukin (IL)-22, a novel human cytokine that signals through the interferon receptor-related proteins CRF2-4 and IL-22R," *J. Biol. Chem.* 275(40):31335-31339.
Xing, W. et al. (Nov. 2011, e-pub Aug. 16, 2011). "Hepatoprotective Effects of IL-22 on Fulminant Hepatic Failure Induced By D-Galactosamine and Lipopolysaccharide in Mice," Cytokine 56(2):174-179. (Abstract Only).
Yamada, A. et al. (Feb. 21, 2016). "Role of Regulatory T Cell in the Pathogenesis of Inflammatory Bowel Disease," World J Gastroenterol 22(7):2195-2205.
Yamaguchi, K. et al. (Jun. 2007). "Inhibiting Triglyceride Synthesis Improves Hepatic Steatosis but Exacerbates Liver Damage and Fibrosis in Obese Mice with Nonalcoholic Steatohepatitis," *Hepatology* 45(6):1366-1374.
Yang, L. et al. (Aug. 2010; e-published on Apr. 21, 2010). "Amelioration of High Fat Diet Induced Liver Lipogenesis and Hepatic Steatosis by Interleukin-22," *Journal of Hepatology* 53(2):339-347.
Yang, R. et al. (Nov. 2012). "MR Imaging of Acute Pancreatitis: Correlation of Abdominal Wall Edema with Severity Scores," *European Journal of Radiology* 81(11):3041-3047.
Yasuda. (1993). *Biomedicine and Therapeutics* 27(10):1221-1223, (English translation of the Introduction only).
Yelton, M.M. et al. (Mar. 1, 1984). "Transformation of *Aspergillus nidulans* by Using a trpC Plasmid," *Proc. Natl. Acad. Sci. USA* 81(5):1470-1474.
Yokoyama, W.M. (Mar. 2006) "How Do Natural Killer Cells Find Self to Achieve Tolerance?" Immunity. 24(3):249-257.
You, M. et al. (Jul. 2004). "Recent Advances in Alcoholic Liver Disease-II. Minireview: Molecular Mechanisms of Alcoholic Fatty Liver," *Am J. Gastrointest Liver Physiol.* 287:G1-G6.
Youdim, A. et al. (Jan. 2018). "Metabolic Syndrome," Merck Manual, four pages.
Yui, S. et al. (Apr. 2012; e-published on Mar. 11, 2012). "Functional Engraftment of Colon Epithelium Expanded in Vitro from a Single Adult Lgr5+ Stem Cell," *Nat Med* 18(4):618-624.
Zamecnik, P.C et al. (Jun. 1, 1986). "Inhibition of Replication and Expression of Human T-Cell Lymphotropic Virus Type III in Cultured Cells by Exogenous Synthetic Oligonucleotides Complementary to Viral RNA," *Proc. Natl. Acad. Sci. USA* 83)12):4143-4146.
Zenewicz, L.A. et al. (2011). "Recent Advances in IL-22 Biology," *International Immunol.* 23(3):159-163.
Zenewicz, L.A. et al. (Dec. 2008). "Innate and Adaptive Interleukin-22 Protects Mice from Inflammatory Bowel Disease," *Immunity* 29(6)947-957.
Zenewicz, L.A. et al. (Oct. 2007, e-pub. Oct. 4, 2007). "Interleukin-22 but Not Interleukin-17 Provides Protection to Hepatocytes during Acute Liver Inflammation," *Immunity* 27:647-659.
Zhang, Y. et al. (Aug. 2010). "Solid Organ Translplant-Associated Acute Graft-Versus-Host Disease," Arch Pathol Lab Med. 134: 1220-1224.
Zhao, K. et al. (Dec. 2013, e-pub May 20, 2013). "The Identification and Characteristics of IL-22-Producing T Cells in Acute Graft-Versus-Host Disease Following Allogeneic Bone Marrow Transplantation," *Immunobiology.* 218(12):1505-1513.

Zheng, X.X. et al. (1995). "Administration of Noncytolytic IL-10/ Fc in Murine Models of Lipopolysaccharide-Induced Septic Shock and Allogeneic Islet Transplantation," *J. Immunol.* 154(10):5590-5600.
Zheng, Y. et al. (Feb. 8, 2007, e-pub. Dec. 24, 2006). "Interleukin-22, a $T_H17$ Cytokine, Mediates IL-23-Induced Dermal Inflammation and Acanthosis," *Nature* 445:648-651.
Zheng, Y. et al. (Mar. 2008, e-pub. Feb. 10, 2008). "Interleukin-22 Mediates Early Host Defense Against Attaching and Effacing Bacterial Pathogens," *Nat Med* 14:282-289.
Zheng, Y.H. et al. (Feb. 28, 2019, e-pub. Feb. 15, 2019). "IL-22/ IL-22R1 Axis is Involved in Myocardial Injury of a Mouse Cecal Ligation and Puncture Model," American Journal of Translational Research 2(11):998-1008.
Zhou, W. J. et al. (Sep. 5, 2013). "Induction of Intestinal Stem Cells by R-Spondin 1 and Slit2 Augments Chemoradioprotection," *Nature* 501:107-111, 16 pages.
Zhu, H. et al. (Nov. 12, 2004, e-pub. Oct. 2, 2004). "STAT3 Induces Anti-Hepatitis C Viral Activity in Liver Cells," *Biochem. Biophys. Res. Commun.* 324(2):518-528.
Zhu, Q. et al. (Nov. 2008). "Expression of rhEPO-L-Fc Fusion Protein and Analysis of its Bioactivity and Pharmacokinetics," *Sheng Wu Gong Cheng Xue Bao* 24(11):1874-1879 (English Abstract).
Zwarycz, B. et al. (2019). "IL22 Inhibits Epithelial Stem Cell Expansion in an Ileal Organoid Model," Cellular and Molecular Gastroenterology and Hepatology 7(1):1-17.
Guiddir, T. et al. (2014). "Anti-TNF-A Therapy May Cause Neonatal Neutropenia," Pediatrics. 134(4):e1189-1193.
Han, L. et al. (2019). "Intestinal Microbiota Can Predict Acute Graft-Versus-Host Disease Following Allogeneic Hematopoietic Stem Cell Transplantation," Biology of Blood and Marrow Transplantation 25(10):1944-1955.
International Search Report and Written Opinion dated Apr. 29, 2021 for International Application No. PCT/CN2021/076929, filed on Feb. 19, 2021, sixteen pages.
International Search Report and Written Opinion dated May 14, 2021 for International Application No. PCT/CN2021/076519, filed on Feb. 10, 2021, sixteen pages.
International Preliminary Report on Patentability dated Aug. 23, 2022, dated Apr. 29, 2021 for International Application No. PCT/ CN2021/076929, filed on Feb. 19, 2021, 6 pages.
International Preliminary Report on Patentability dated Aug. 23, 2022, dated May 14, 2021 for International Application No. PCT/ CN2021/076519, filed on Feb. 10, 2021, 6 pages.
Kong, Q. et al. (Oct. 11, 2012). "Increased Expressions of IL-22 and Th22 Cells in the Coxsackievirus B3-Induced Mice Acute Viral Myocarditis," Virol. J. 9(232):1-10.
Levine, J.E. et al. (Jan. 1, 2015). "A Prognostic Score For Acute Graft-Versus-Host Disease Based on Biomarkers: A Multicentre Study," Lancet Haematol. 2(1):e21-e29.
Lindemans, C. et al. (Dec. 24, 2015). "Interleukin-22 Promotes Intestinal-Stem-Cell-Mediated Epithelial Regeneration," Nature 528(7583):560-564.
NIH (Apr. 2, 2015). "Study of IL-22 IgG2-Fc (F-652) for Subjects With Grade II-IV Lower GI aGVHD," ClinicalTrials.gov, No. NCT02406651, 13 pages, retrieved on Jun. 27, 2022, from https:// www.clinicaltrials.gov/ct2/show/results/NCT02406651?term= NCT02406651&draw=2&rank=1&view=results.
Pociask, D. et al. (Apr. 2013). "IL-22 is Essential For Lung Epithelial Repair Following Influenza Infection," Am. J. Pathol. 182(4):1286-1296.
Ponce, D.M. et al. (2020). "A Phase 2 Study of F-652, a Novel Tissue-Targeted Recombinant Human Interleukin-22 (IL-22) Dimer, for Treatment of Newly Diagnosed Acute Gvhd of the Lower GI Tract," Biol Blood Marrow Transplant. 26(3):S51-S52.
U.S. Appl. No. 17/799,627, filed Aug. 12, 2022, by Yang et al. (Copy not submitted herewith pursuant tc the waiver of 37 C.F.R. § 1.98 (a)(2)(iii) issued by the Office on Sep. 21, 2004.).
U.S. Appl. No. 17/800,827, filed Aug. 18, 2022, by Daley et al. (Copy not submitted herewith pursuant to the waiver of 37 C.F.R. § 1.98 (a)(2)(iii) issued by the Office on Sep. 21, 2004 ).

(56) References Cited

OTHER PUBLICATIONS

Xiang, X. et al. (2011). "IL-22 and Non-ELR-CXC Chemokine Expression in Chronic Hepatitis B Virus-Infected Liver," Immunol. Cell Biol. 90(6):1-9.

Yazji, I. et al. (May 6, 2013). "Endothelial TLR4 Activation Impairs Intestinal Microcirculatory Perfusion In Necrotizing Enterocolitis Via Enos-NO-Nitrite Signaling," Proceedings of the National Academy of Sciences 110(23):9451-9456.

Zani, A. et al. (2015, e-pub. Oct. 26, 2014). "International Survey on the Management of Necrotizing Enterocolitis," European Journal of Pediatric Surgery 25(01):27-33.

Zhang, H.M. et al. (Nov. 30, 2017). "Endothelial Glycocalyx in Diagnosis and Treatment of Sepsis," Occupation and Health 33(22):3158-3162 (English Abstract Only).

* cited by examiner

USE OF IL-22 DIMER IN MANUFACTURE OF A MEDICAMENT FOR INTRAVENOUS ADMINISTRATION

RELATED APPLICATIONS

This application is a continuation patent application of U.S. patent application Ser. No. 15/034,859, filed May 5, 2016, now issued as U.S. Pat. No. 10,543,169, which is a National Phase application under 35 U.S.C. § 371 of International Application No. PCT/CN2014/090520, filed Nov. 6, 2014, which claims priority benefit to Chinese Patent Application No. 201310549838.1, filed Nov. 7, 2013, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 720622001101SEQLIST.TXT, date recorded: Dec. 5, 2019, size: 22 KB).

FIELD OF INVENTION

This invention relates to the area of biological and medical technologies, in particular, this invention relates to the use of IL-22 dimer in the manufacture of a medicament for intravenous administration.

BACKGROUND

Interleukin-22 (IL-22), also known as IL-10 related T cell-derived inducible factor (IL-TIF), is a glycoprotein expressed in and secreted from activated T cells and natural killer cells (NK cells). Activated T cells are mainly CD4+ cells, especially CD28 pathway activated $T_h1$ cells, $T_h17$ cells and $T_h22$ cells, among others. The expression of IL-22 mRNA was originally identified in IL-9 simulated T cells and mast cells in murine, as well as Concanavilin A (Con A) stimulated spleen cells (Dumoutier, et al., J. Immunology, 164:1814-1819, 2000). The human IL-22 mRNA is mainly expressed in peripheral T cells upon stimulation by anti-CD3 or Con A. Feng et al. reported Interleukin-22 ameliorates cerulein-induced pancreatitis in mice(Int. J. Biol. Sci, 8(2), 249-257, 2012).

The disclosures of all publications, patents, patent applications and published patent applications referred to herein are hereby incorporated herein by reference in their entirety.

SUMMARY OF INVENTION

It is an object of the present invention to provide a use of IL-22 dimer in the manufacture of a medicament for intravenous administration.

In one aspect of the present invention, a use of interleukin-22 (IL-22) dimer in the manufacture of a medicament for intravenous administration is provided.

In some embodiments, the medicament is used for the treatment of a disease selected from the group consisting of: metabolic disease, fatty liver, viral hepatitis, MODS, neurological disorder, and pancreatitis.

In some embodiments, the IL-22 dimer is shown as Formula I:

M1-L-M2              I wherein,
M1 is a first monomer of IL-22,
M2 is a second monomer of IL-22, and
L is a linker connecting said first monomer and said second monomer and disposed therebetween.

In some embodiments, the IL-22 dimer retains the biological activity of IL-22 and has a serum half-life of longer than twice of that of either the first or the second monomer.

In some embodiments, the serum half-life of the IL-22 dimer is longer than three, five, or ten times of that of the first and/or the second monomer.

In a preferred embodiment, the linker L is selected from the group consisting of:
(i). a short peptide comprising 3 to 50 amino acids; and
(ii). a polypeptide of Formula II:

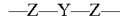

—Z—Y—Z—           II wherein,
Y is a carrier protein,
Z is nothing, or a short peptide(s) comprising 1 to 30 amino acids, and
"-" is a chemical bond or a covalent bond.

In some embodiments, the "-" is a peptide bond.

In some embodiments, Z is 5-50 amino acid residues in length.

In some embodiments, Z comprises the sequence of SEQ ID NO: 1 or SEQ ID NO: 10.

In some embodiments, Z has the sequence of SEQ ID NO: 1 or SEQ ID NO: 10.

In some embodiments, the carrier protein contains at least two cysteines capable of forming intermolecular disulfide bonds.

In some embodiments, the carrier protein is disposed at the N-terminal of IL-22 monomer.

In some embodiments, the carrier protein is disposed at the C-terminal of IL-22 monomer.

In some embodiments, the carrier protein is albumin or Fc fragment of human IgG.

In some embodiments, Fc fragment contains CH2 and CH3 domains.

In some embodiments, Fc fragment comprises the sequence of SEQ ID NO: 2 or SEQ ID NO: 9.

In some embodiments, Fc fragment has the sequence of SEQ ID NO: 2 or SEQ ID NO: 9.

In some embodiments, the IL-22 dimer is formed by two monomeric subunits wherein each monomeric subunit comprises an IL-22 domain, a dimerization domain and optionally a linker connecting the IL-22 domain and the dimerization domain.

In some embodiments, the IL-22 domain is IL-22 monomer, the dimerization domain comprises Fc fragment of human immunoglobulin (such as IgG1, IgG2, IgG3, or IgG4), the optional linker is a peptide connecting the IL-22 monomer and Fc fragment, and the dimer is formed by the connection of two dimerization domains (such as Fc Fragment) via one or more disulfide bond(s).

In some embodiments, the number of said disulfide bond is 2-4.

In some embodiments, the monomeric subunit of each IL-22 dimer comprises an amino acid sequence selected from SEQ ID NO: 4 and SEQ ID NOs: 6-8.

In some embodiments, the first monomer and the second monomer of the IL-22 dimer are identical.

In some embodiments, the first monomer and the second monomer are different.

In some embodiments, the biological activity of the IL-22 dimer is selected from one or more biological activities in a group consisting of:
(a) reducing the levels of amylase and/or lipase in vivo,
(b) ameliorating pancreatic edema in vivo,
(c) inhibiting necrosis of acinar cells and/or adipocytes in pancreas in vivo,
(d) ameliorating the infiltration of inflammatory cells in pancreas in vivo.

In some embodiments, the medicament is administered by the following ways: administering the IL-22 dimer at the amount of about 2 μg/kg to about 200 μg/kg, preferably at the amount of about 5 μg/kg to about 80 μg/kg IL-22 dimer, more preferably at the amount of about 10 μg/kg to about 45 μg/kg IL-22 dimer.

In a second aspect of the present invention, there is provided a method of administering an IL-22 dimer to an individual, comprising intravenously administering to the individual an effective amount of an IL-22 dimer, wherein the amount of the IL-22 dimer is about 2 μg/kg to about 200 μg/kg.

In a third aspect of the present invention, there is provided a method of treating diseases in an individual, comprising intravenously administering to the individual an effective amount of an IL-22 dimer, wherein the amount of the IL-22 dimer is about 2 μg/kg to about 200 μg/kg.

In some embodiments, the amount of the IL-22 dimer is about 5 μg/kg to about 80 μg/kg.

In some embodiments, the amount of the IL-22 dimer is about 10 μg/kg to about 45 μg/kg.

In some embodiments, the IL-22 dimer is administered no more than about once every week.

In some embodiments, the IL-22 dimer is administered no more than about once every month.

In some embodiments, the IL-22 dimer is administered no more than about once every three months.

In some embodiments, the IL-22 dimer comprises two monomeric subunits, wherein each monomeric subunit comprises an IL-22 domain and a dimerization domain.

In some embodiments, each monomeric subunit comprises an IL-22 domain linked to a dimerization domain via an optional linker sequence.

In some embodiments, the linker sequence is about 6 to about 30 amino acids.

In some embodiments, the linker sequence comprises the sequence of SEQ ID NO: 1.

In some embodiments, the linker sequence has the sequence of SEQ ID NO: 1.

In some embodiments, the dimerization domain comprises at least two cysteines capable of forming intermolecular disulfide bonds.

In some embodiments, the dimerization domain comprises at least a portion of the Fc fragment.

In some embodiments, the Fc fragment comprises CH2 and CH3 domains.

In some embodiments, the Fc fragment comprises the sequence of SEQ ID NO: 2.

In some embodiments, the Fc fragment has the sequence of SEQ ID NO: 2.

In some embodiments, the IL-22 domain of each monomeric subunit has the sequence of SEQ ID NO: 3.

In some embodiments, the each monomeric subunit has the sequence selected from SEQ ID NO: 4 and SEQ ID NOs: 6-8.

In some embodiments, the disease is selected from the group consisting of metabolic disease, fatty liver, viral hepatitis, MODS, neurological disorder, and pancreatitis.

In some embodiments, the individual is human.

It is clear for a skilled person in the art that, the technical features mentioned above and discussed in the examples below of the present invention could be combined with each other to result in a new or even better technical solution. Hence this invention should not be construed as limited to the embodiments set forth herein.

BRIEF DESCRIPTION OF FIGURES

As illustrated in FIG. 2A, the oval-shaped object labeled with "C" represents a carrier protein wherein the IL-22 is disposed at the N-terminal of the carrier protein. As illustrated in FIG. 2B, the half oval-shaped object labeled with "Fc" represents an Fc fragment which is a dimerization domain, showing a dimer is formed by the coupling of two Fc fragments via disulfide bond(s).

As illustrated in FIG. 3A, the oval-shaped object labeled with "C" represents a carrier protein wherein the IL-22 is disposed at the C-terminal of the carrier protein. As illustrated in FIG. 3B, the half oval-shaped object labeled with "Fc" represents an Fc fragment which is a dimerization domain, showing a dimer is formed by the coupling of two Fc fragments via disulfide bond(s).

Figure 1:
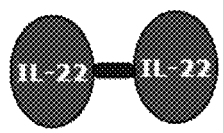
FIG. 1 is an illustration of an exemplary IL-22 dimer according to the present invention. In the figure, "-" represents a linker and the oval-shaped object labeled with "IL-22" represents an IL-22 monomer.
Figure 2A:
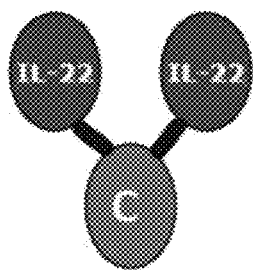
FIGS. 2A and 2B are illustrations of exemplary IL-22 dimers according to the present invention. In the figures, "-" represents an amino acid linker and the oval-shaped object labeled with "IL-22" represents an IL-22 monomer.
Figure 2B:
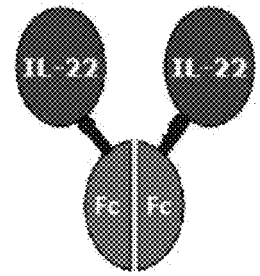
Figure 3A:
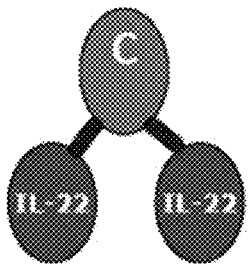
FIGS. 3A and 3B are illustrations of exemplary IL-22 dimers according to the present invention. In the figures, "-" represents an amino acid linker, the oval-shaped object labeled with "IL-22" represents an IL-22 monomer.
Figure 3B:
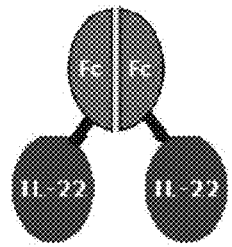

DETAILED DESCRIPTION OF THE
INVENTION

Upon an extensive and thorough study, the inventors have surprisingly found that IL-22 dimer has an outstanding effect in the manufacture of a medicament for intravenous administration. On this basis, this invention is achieved.

The present application provides methods of administering an IL-22 dimer by following a specific dosing regimen. The present application is based on the surprising finding that an IL-22 dimer, specifically, a dimeric complex of IL-22-Fc monomers, shows significantly lower toxicity when administered intravenously as compared to subcutaneous administration. Specifically, when a dimeric complex of IL-22-Fc monomers is administered subcutaneously to an individual at a dosage of about 2 µg/kg, delayed adverse events of the injection site, such as dry skin, erythema and nummular eczema were observed after dosing. On the other hand, the dimeric complex of IL-22-Fc monomers administered intravenously to an individual demonstrated excellent safety profile. No adverse event of the injection site and skin was observed at doses of about 2 or 10 µg/kg. Even at doses as high as 30-45 µg/kg, only limited adverse events such as dry skin, eye pruritus, erythematous rash were observed. Furthermore, the administration of IL-22 dimer does not lead to an increased serum level of an inflammatory cytokine in human.

Thus, the present application in one aspect provides methods of administering an IL-22 dimer to an individual (such as a human individual), comprising intravenously administering to the individual an effective amount of an IL-22 dimer, wherein the amount of the IL-22 dimer is about 2 µg/kg to about 200 µg/kg (such as about 10 µg/kg to about 45 µg/kg). In another aspect, there is provided a method of treating a disease in an individual (such as a human individual), comprising intravenously administering to the individual an effective amount of an IL-22 dimer, wherein the amount of the IL-22 dimer is about 2 µg/kg to about 200 µg/kg (such as about 10 µg/kg to about 45 µg/kg). Also provided are kits, unit dosages, and articles of manufacture for use in any one of the methods described herein.

Methods of the Present Invention

The methods described herein comprise administering an effective amount of an IL-22 dimer to an individual via intravenous administration. Suitable dosage of the IL-22 dimer includes, for example, about 2 µg/kg to about 200 µg/kg, including for example about 5 µg/kg to about 80 µg/kg, about 10 µg/kg to about 45 µg/kg, or about 30 to about 40 µg/kg. In some embodiments, the IL-22 dimer is administered intravenously at the dose of at least about any of 10 µg/kg, 20 µg/kg, 30 µg/kg, 40 µg/kg, or 50 µg/kg. In some embodiments, the IL-22 dimer is administered intravenously at the dose of no more than about any of 10 µg/kg, 20 µg/kg, 30 µg/kg, 40 µg/kg, or 50 µg/kg.

In some embodiments, there is provided a method of administering an IL-22 dimer to an individual (such as a human individual), comprising intravenously administering to the individual an IL-22 dimer, wherein the amount of the IL-22 dimer is about 10 µg/kg to about 45 µg/kg. In some embodiments, the amount of the IL-22 dimer is about 10 µg/kg to about 15 µg/kg, about 15 µg/kg to about 20 µg/kg, about 20 µg/kg to about 25 µg/kg, about 25 µg/kg to about 30 µg/kg, about 30 µg/kg to about 45 µg/kg. In some embodiments, the IL-22 dimer is administered at about 20 µg/kg to about 40 µg/kg, including for example about 30 µg/kg to about 35 µg/kg.

In some embodiments, the IL-22 dimer is administered once every week. In some embodiments, the IL-22 dimer is administered once every 2, 3, 4, 5, 6, 7, 8, 9, 10, 11, 12, or 24 weeks. In some embodiments, the IL-22 dimer is administered once every 1, 2, 3, 4, 5, 6, 7, 8, 9, 10, or 12 months. In some embodiments, the IL-22 dimer is administered only once. In some embodiments, the IL-22 dimer is administered no more frequently than once every week, once every month, once every two months, or once every six months.

In some embodiments, there is provided a method of administering an IL-22 dimer to an individual (such as a human individual), comprising intravenously administering to the individual an effective amount of an IL-22 dimer, wherein the amount of the IL-22 dimer is about 2 µg/kg to about 200 µg/kg (such as about 10 µg/kg to about 45 µg/kg). In some embodiments, there is provided a method of administering an IL-22 dimer to an individual (such as a human individual), comprising intravenously administering to the individual an effective amount of an IL-22 dimer, wherein the amount of the IL-22 dimer is about 2 µg/kg to about 200 µg/kg (such as about 10 µg/kg to about 45 µg/kg), wherein the IL-22 dimer is administered by intravenous push (IVP). In some embodiments, there is provided a method of administering an IL-22 dimer to an individual (such as a human individual, comprising intravenously administering to the individual an effective amount of an IL-22 dimer, wherein the amount of the IL-22 dimer is about 2 µg/kg to about 200 µg/kg (such as about 10 µg/kg to about 45 µg/kg), wherein the IL-22 dimer is administered by intravenous infusion. In some embodiments, there is provided a method of administering an IL-22 dimer to an individual (such as a human individual, comprising intravenously administering to the individual an effective amount of an IL-22 dimer, wherein the amount of the IL-22 dimer is about 2 µg/kg to about 200 µg/kg (such as about 10 µg/kg to about 45 µg/kg), wherein the IL-22 dimer is administered by continuous intravenous infusion.

In some embodiments, there is provided a method of administering an IL-22 dimer to an individual (such as a human individual), comprising intravenously administering to the individual an effective amount of an IL-22 dimer, wherein the amount of the IL-22 dimer is about 2 µg/kg to about 200 µg/kg (such as about 10 µg/kg to about 45 µg/kg). In some embodiments, there is provided a method of administering an IL-22 dimer to an individual (such as a human individual), comprising intravenously administering to the individual an effective amount of an IL-22 dimer, wherein the amount of the IL-22 dimer is about 2 µg/kg to about 200 µg/kg (such as about 10 µg/kg to about 45 µg/kg), wherein the IL-22 dimer is administered at least about once a week, for example at least about 2×, 3×, 4×, 5×, 6×, or 7× a week. In some embodiments, there is provided a method of administering an IL-22 dimer to an individual (such as a human individual), comprising intravenously administering to the individual an effective amount of an IL-22 dimer, wherein the amount of the IL-22 dimer is about 2 µg/kg/day to about 200 µg/kg/day (such as about 10 µg/kg/day to about 45 µg/kg/day), wherein the IL-22 dimer is administered continuously, for example via an infusion pump. In some embodiments, there is provided a method of administering an IL-22 dimer to an individual (such as a human individual), comprising intravenously administering to the individual an effective amount of an IL-22 dimer, wherein the amount of the IL-22 dimer is about 2 µg/kg to about 200

μg/kg (such as about 10 μg/kg to about 45 μg/kg), wherein the IL-22 dimer is administered no more than about once a week, for example no more than about any of once every two weeks, once every three weeks, once every four weeks, once every five weeks, once every six weeks, once every eight weeks, once every ten weeks, once every twelve weeks. In some embodiments, there is provided a method of administering an IL-22 dimer to an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg), wherein the IL-22 dimer is administered no more than about once a month, for example no more than about any of once every two months, once every three months, once every four months, once every five months, once every six months, once every seven months, once every eleven months, once every twelve months. In some embodiments, the IL-22 dimer is administered no more than about once every 2, 3, 4, 5, 6, or 7 years.

The methods described herein can be useful for preventing and/or treating various diseases including but not limited to, metabolic disease, fatty liver, viral hepatitis, MODS (multiple organ dysfunction syndrome), neurological disorder, and pancreatitis.

In some embodiments, there is provided a method of treating a disease in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). As used herein, the term "the individual to be treated" or "individual" refers to a mammal, such as human. An individual includes, but is not limited to, human, bovine, horse, feline, canine, rodent, or primate. In some embodiments, the individual is human.

In some embodiments, the individual to be treated is 16 years of age or younger, 18 years of age or younger, 25 years of age or younger, 35 years of age or younger, 45 years of age or younger, 55 years of age or younger, 65 years of age or younger, or 75 years of age or younger. In some embodiments, individual to be treated is 16 years of age or older, 18 years of age or older, 25 years of age or older, 35 years of age or older, 45 years of age or older, 55 years of age or older, 65 years of age or older, or 75 years of age or older.

In some embodiments, the individual administered with the IL-22 dimer does not show injection site reactions. In some embodiments, the individual administered with the IL-22 dimer does not show one or more of: dry skin, erythema, or nummular eczema, and/or significant abnormalities of the other safety evaluation indexes, such as physical examination, laboratory test, body weight, vital signs, electrocardiogram, and abdomen ultrasound.

In some embodiments, there is provided a method of treating a metabolic disease in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). Metabolic diseases that can be treated with the methods described herein include, but are not limited to, diabetes, hyperlipidemia and hyperglycemia. In some embodiments, there is provided a method of treating obesity in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, the IL-22 dimer is administered by intravenous infusion. In some embodiments, the IL-22 dimer is administered by intravenous push. In some embodiments, the IL-22 is administered by continuous intravenous infusion.

In some embodiments, there is provided a method of treating hyperlipidemia in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, there is provided a method of losing weight in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, the IL-22 dimer is administered by intravenous infusion. In some embodiments, the IL-22 dimer is administered by intravenous push. In some embodiments, the IL-22 is administered by continuous intravenous infusion.

In some embodiments, there is provided a method of improving glucose tolerance in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, there is provided a method of reducing adipocyte size in an individual (such as a human individual, for example an overweight human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, the IL-22 dimer is administered by intravenous infusion. In some embodiments, the IL-22 dimer is administered by intravenous push. In some embodiments, the IL-22 is administered by continuous intravenous infusion. In some embodiments, there is provided a method of treating fatty liver in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, there is provided a method of reducing deposition of triglyceride in an individual (such as human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, there is provided a method of reducing steatosis in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, the IL-22 dimer is administered by intravenous infusion. In some embodiments, the IL-22 dimer is administered by intravenous push. In some embodiments, the IL-22 is administered by continuous intravenous infusion.

Fatty liver is a disease in which excessive amounts of lipids accumulate in the liver cells. Normally lipids account for 3%-4% of the total weight of the liver. If the amount of lipid goes beyond 5%, a fatty liver forms. Lipids may comprise up to 40%-50% of the liver weight in severe fatty liver diseases. Fatty liver mainly comes from the disorder of lipid metabolism of the liver. The main form of lipid in the liver is triglyceride, which is characterized by macrovesicular steatosis. Fatty liver can lead to fibrosis of liver, cirrhosis and hepatocellular carcinoma. In some embodiments, the fatty liver to be treated is alcoholic fatty liver disease (AFLD), which is caused by excessive alcohol intake (greater than 20 g ethanol per day).

In some embodiments, the fatty liver to be treated is non-alcoholic fatty liver disease (NAFLD), including non-alcoholic fatty liver disease and steatohepatitis. In some embodiments, the NAFLD is obesity fatty liver, diabetic fatty liver, overnutritional or malnutritional fatty liver, fatty liver of pregnancy, drug induced fatty liver, fatty liver of hyperlipidemia, and fatty liver of middle-aged and elderly. In some embodiments, the NAFLD is induced by metabolic syndrome including insulin resistance, lipid metabolism dysfunction and etc. In some embodiments, the NAFLD is induced indirectly by medicaments such as glucocorticoid, hormones, Tamoxifen, Methotrexate, Zidovudine, Amiodarone, acetylsalicylic acid (ASA), tetracycline, Didanosine, cocaine, perhexiline, hypervitaminosis A, Diltizem; toxin such as, *Amanita phalloides Lepiota*, Petrochemicals, phosphate, *Bacillus Cereus* toxin, organic solvent; indirect diseases induced such as, lipodystrophy, dysbetalipoproteinemia, Weber-Christian disease, Wolman's disease, acute fatty liver of pregnancy, Reye's syndrome; idiopathic immuno-disease such as, inflammatory bowel disease (IBD), arthritis, lupus erythematosus; viral infection such as HIV, HBV; bacterial infections; or severe weight loss such as, starvation, gastric bypass, intestinal operation. In some embodiments, there is provided a method of treating viral hepatitis in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). Viral hepatitis is an inflammation of the liver caused by hepatitis A, B, C, D, or E virus. In some embodiments, the viral hepatitis is any of hepatitis A, hepatitis B, hepatitis C, hepatitis D, hepatitis D, and hepatitis E. In some embodiments, the viral hepatitis is acute viral hepatitis. In some embodiments, the viral hepatitis is chronic hepatitis. In some embodiments, the IL-22 dimer is administered by intravenous infusion. In some embodiments, the IL-22 dimer is administered by intravenous push. In some embodiments, the IL-22 is administered by continuous intravenous infusion.

In some embodiments, there is provided a method of preventing the development of cirrhosis, liver failure, or liver cancer in an individual (such as a human individual) having viral hepatitis, comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, the IL-22 dimer is administered by intravenous infusion. In some embodiments, the IL-22 dimer is administered by intravenous push. In some embodiments, the IL-22 is administered by continuous intravenous infusion.

In some embodiments, there is provided a method of preventing liver tissue damage in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, there is provided a method of maintaining or decreasing the level of a hepatic enzyme (such as transaminase, for example aspartate aminotransferase or alanine aminotransferase) in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, the IL-22 dimer is administered by intravenous infusion. In some embodiments, the IL-22 dimer is administered by intravenous push. In some embodiments, the IL-22 is administered by continuous intravenous infusion.

In some embodiments, there is provided a method of treating multiple organ dysfunction syndrome (MODS) in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, the IL-22 dimer is administered by intravenous infusion. In some embodiments, the IL-22 dimer is administered by intravenous push. In some embodiments, the IL-22 is administered by continuous intravenous infusion.

Multiple organ dysfunction syndrome (MODS), previously known as multiple organ failure (MOF), is altered organ function in an acutely ill patient such that homeostasis cannot be maintained without medical intervention. MODS usually results from uncontrolled inflammatory response, which is triggered by infection, injury (accident or surgery), hypoperfusion and/or hypermetabolism. The uncontrolled inflammatory response will lead to SIRS or sepsis. SIRS is an inflammatory state affecting the whole body. It is one of several conditions related to systemic inflammation, organ dysfunction, and organ failure. SIRS is a subset of cytokine storm, in which there is abnormal regulation of various cytokines. SIRS is also closely related to sepsis. When SIRS is due to an infection, it is considered as sepsis. Noninfectious causes of SIRS include trauma, burns, pancreatitis, ischemia and hemorrhage. Sepsis is a serious medical condition characterized by a whole-body inflammatory state. Sepsis can lead to septic shock, multiple organ dysfunction syndrome and death. Both SIRS and sepsis could ultimately progress to MODS.

Thus, in some embodiments, there is provided a method of treating SIRS in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, there is provided a method of treating MOF in an individual (such as human), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, there is provided a method of treating sepsis in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, there is provided a method of treating liver failure in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, the MODS, SIRS, MOF, sepsis, or liver failure is caused by trauma, which includes, but is not limited to, traffic accident, burns, heart attack, and severe infective diseases.

In some embodiments, there is provided a method of treating a neurological disorder in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). Suitable neurological diseases that can be treated with the methods of the present application include, but are not limited to, stroke, spinal cord injury, diseases associated with injured blood/brain barrier, and neurodegenerative diseases such as Alzheimer's disease, Parkinson's disease, Huntington's disease, amyotrophic lateral sclerosis, spinal muscular atrophy, spinal cerebellar and ataxias.

In some embodiments, there is provided a method of treating pancreatitis in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, the pancreatitis is selected from the group consisting of: acute pancreatitis, chronic pancreatitis, alcoholic pancreatitis, recurrent pancreatitis, bile reflux pancreatitis, interstitial pancreatitis, necrotizing pancreatitis, post ERCP pancreatitis.

IL-22

As used herein, the term "Interleukin-22" or "IL-22" refers to a protein, which (a) has essentially the same amino acid sequence as the human/murine IL-22 as described by Dumoutier et al. in U.S. Pat. No. 6,359,117 and (b) the same biological activity as natural IL-22. IL-22 of the present invention includes but is not limited to human IL-22, recombinant human IL-22, murine IL-22 and/or recombinant murine IL-22.

Specifically, Interleukin-22 (IL-22), also known as IL-10 related T cell-derived inducible factor (IL-TIF), is a glycoprotein expressed in and secreted from activated T cells and natural killer cells (NK cells). Activated T cells are mainly CD4+ cells, especially CD28 pathway activated $T_h1$ cells, $T_h17$ cells and $T_h22$ cells, among others. The expression of IL-22 mRNA was originally identified in IL-9 simulated T cells and mast cells in murine, as well as Concanavilin A (Con A) stimulated spleen cells (Dumoutier, et al., J. Immunology, 164:1814-1819, 2000). The human IL-22 mRNA is mainly expressed in peripheral T cells upon stimulation by anti-CD3 or Con A.

Native IL-22 precursor peptide consists of 179 amino acid residues, while the mature peptide consists of 146 amino acid residues. Dumoutier first reported the IL-22 cloned DNA sequences of mouse and human (Dumoutier, et al., 2000; U.S. Pat. Nos. 6,359,117 and 6,274,710). IL-22 is mainly expressed in activated T cells(especially Th17 cells), the lectin-stimulated spleen cells (Dumoutier J I, 2000), IL-2/IL-12-stimulated NK cells (Wolk, K et al., J. Immunology, 168:5379-5402, 2002), and in a number of organs and tissues, including gut, liver, stomach, kidney, lung, heart, thymus, spleen, upon LPS stimulation, in which an increase of the expression of IL-22 in those organs and tissues can be measured. IL-22 expresses its biological function through the combination of IL-22R1 receptor and IL-10R2 receptor. IL-22R1 is a receptor specific to IL-22 and is expressed in skin, kidney, the digestive system (pancreas, small intestine, liver, large intestine, colon), and the respiratory system (lung, bronchi). Published researches demonstrated that IL-22 is an immuno-modulator.

IL-22 Dimer

The structure of the IL-22 dimer of the present invention is exemplified as Formula I. FIGS. 1-3B illustrate the representative structures of the IL-22 dimer of the present invention, in which the carrier protein includes but is not limited to Fc fragment of human IgG (such as IgG1, IgG2, IgG3 or IgG 4), or human albumin.

In some embodiments, the IL-22 dimer of the present invention comprises two monomeric subunits, in which each monomeric subunit comprises an IL-22 domain and a dimerization domain. Each of monomeric subunits comprises an IL-22 domain linked to a dimerization domain via an optional linker sequence. The IL-22 domain can be at the C terminus or N terminus of the dimerization domain. The carrier protein of the IL-22 dimer is formed by two dimerization domains via dimerization.

An amino acid sequence of the IL-22 dimer is shown in SEQ ID NO: 5 in which amino acid residues 1-146 represent IL-22, amino acid residues 147-162 represent the linker, and residues 163-308 represent another IL-22.

An amino acid sequence of an IL-22 monomer with Fc fragment, which is used to form the IL-22 dimer of this embodiment, is shown in SEQ ID NO: 4 in which amino acid residues 1-146 represent an IL-22, amino acid residues 147-162 represent the linker, and residues 163-385 represent Fc fragment of human IgG2. A dimer is formed by the two IL-22 monomers with Fc fragment via the coupling of the Fc fragments.

An amino acid sequence of an IL-22 monomer with Fc fragment, which is used to form the IL-22 dimer of this embodiment, is shown in SEQ ID NO: 6 in which amino acid residues 1-146 represent an IL-22, amino acid residues 147-152 represent the linker, and residues 153-375 represent Fc fragment of human IgG2. A dimer is formed by the two IL-22 monomers with Fc fragment via the coupling of the Fc fragments.

An amino acid sequence of an IL-22 monomer with Fc fragment, which is used to form the IL-22 dimer of this embodiment, is shown in SEQ ID NO: 7 in which amino acid residues 1-223 represent Fc fragment of human IgG2, amino acid residues 224-239 represent the linker, and residues 240-385 represent an IL-22. A dimer is formed by the two IL-22 monomers with Fc fragment via the coupling of the Fc fragments.

An amino acid sequence of an IL-22 monomer with Fc fragment, which is used to form the IL-22 dimer of this embodiment, is shown in SEQ ID NO: 8 in which amino acid residues 1-223 represent Fc fragment of human IgG2, amino acid residues 224-229 represent the linker, and residues 230-375 represent an IL-22. A dimer is formed by the two IL-22 monomers with Fc fragment via the coupling of the Fc fragments.

As used herein and in the claims, the term "linker peptide" or "linker" refers to oligo peptide disposed between one IL-22 monomer and carrier protein, or one IL-22 monomer (or IL-22 domain) and a dimerization domain and connecting the two domains together. There is no special restriction on the length of the linker. A linker is usually 5-50 amino acid residues in length. In general, a linker does not affect or significantly affect the proper fold and conformation formed by the configuration of the two IL-22 monomers. Some examples of linkers include (but are not limited to):

Preferably, the linker contains an amino acid sequence selected from:

(a). an amino acid sequence with 3-16 hydrophobic amino acid residues Gly or Pro, such as Gly-Pro-Gly-Pro-Gly-Pro;

(b). an amino acid sequence encoded by multiple cloning sites. Such sequences usually contain 5-20 amino acid residues, preferably, 10-20 amino acid residues;

(c). an amino acid sequence of a protein other than IL-22 monomer, such as an amino acid sequence of IgG or albumin; and (d). an amino acid sequence comprising any combination of (a), (b), and (c) above.

In one preferred embodiment, the linker has the sequence of GSGGGSGGGGSGGGGS (i.e. amino acid residues of SEQ ID NO: 1) and ASTKGP (i.e. amino acid residues of SEQ ID NO: 10).

In addition, an amino acid sequence not affecting the biological activity of IL-22 monomer can be added to the N-terminal or C-terminal of the fusion protein. In a preferred embodiment, such appended amino acid sequence is beneficial to expression (e.g. signal peptide), purification (e.g. 6×His sequence, the cleavage site of *Saccharomyces cerevisiae* α-factor signal peptide (Glu-Lys-Arg), or enhancement of biological activity of the fusion protein.

In some embodiments, the IL-22 dimer comprises two monomeric subunits, wherein each monomeric subunit comprises an IL-22 domain and a dimerization domain. In some embodiments, the IL-22 domain is fused to the N-terminus of the dimerization domain. In some embodiments, the IL-22 domain is fused to the C-terminus of the dimerization domain. In some embodiments, the IL-22 domain and the dimerization domain are linked via an optional peptide linker (for example a peptide linker of about 5 to about 50 amino acids in length, for example a linker having the sequence of SEQ ID NO: 10). In some embodiments, the dimerization domain of IL-22 dimer comprises leucine zippers.

In some embodiments, the IL-22 dimer comprises two IL-22 monomeric subunits, wherein each monomeric subunit comprises an IL-22 monomer and at least a portion of an immunoglobulin Fc fragment("the Fc fragment", or namely Fc region). In some embodiments, the IL-22 domain is fused to the N-terminus of the Fc fragment. In some embodiments, the IL-22 domain is fused to the C-terminus of the Fc fragment. In some embodiments, the IL-22 domain and the Fc fragment are linked via an optional peptide linker (for example a peptide linker of about 5 to about 50 amino acids in length, for example a linker having the sequence of SEQ ID NO: 1 or SEQ ID NO: 10). In some embodiments, the IL-22 domain has the sequence of SEQ ID NO: 3. In some embodiments, the Fc fragment comprises at least two cysteines capable of forming intermolecular disulfide bonds. In some embodiments, the Fc fragment is truncated at the N-terminus, e.g., lacks the first 1, 2, 3, 4, 5, 6, 7, 8, 9, or 10 amino acids of a complete immunoglobulin Fc domain. In some embodiments, the Fc fragment is of type IgG2. In some embodiments, the Fc fragment is of type IgG4. In some embodiments, the Fc fragment has the sequence of SEQ ID NO: 2 or SEQ ID NO: 9.

In some embodiments, the IL-22 dimer comprises two IL-22 monomeric subunits, wherein each monomeric subunit comprises (for example has) the sequence of any of SEQ ID NO: 4 or SEQ ID NOs: 6-8.

The invention encompasses modifications to the polypeptides described herein, including functionally equivalent proteins which do not significantly affect their properties and variants which have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, non-conservative mutations which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an N-terminal methionyl residue or an epitope tag. Other insertional variants of the IL-22 monomeric subunits include the fusion to the N- or C-terminus of the polypeptide, or a polypeptide which increases the serum half-life of the IL-22 dimer.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. In contrast, non-conservative amino acid substitutions tend to disrupt conformation and function of a protein. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). (See Table 1 below.)

TABLE 1

| Example of amino acid classification | |
| --- | --- |
| Small/Aliphatic residues: | Gly, Ala, Val, Leu, Ile |
| Cyclic Imino Acid: | Pro |
| Hydroxyl-containing Residues: | Ser, Thr |
| Acidic Residues: | Asp, Glu |
| Amide Residues: | Asn, Gln |
| Basic Residues: | Lys, Arg |
| Imidazole Residue: | His |
| Aromatic Residues: | Phe, Tyr, Trp |
| Sulfur-containing Residues: | Met, Cys |

In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., Biochemistry at pp. 13-15, 2nd ed. Lubert Stryer ed. (Stanford University); Henikoff et al., Proc. Nat'l Acad. Sci. USA (1992) 89:10915-10919; Lei et al., J. Biol. Chem. (1995) 270(20): 11882-11886).

It was surprising found that although certain IL-22 dimers have less activities than IL-22 in in vitro assays, they are significantly more active in an in vivo context in treating pancreatitis. For example, in some embodiments, the IL-22 dimer described herein has an EC50 of no less than about 20 ng/mL (including for example no less than about any of 100 ng/mL, 200 ng/mL, 300 ng/mL, 400 ng/mL, or more) in an in vitro cell proliferation assay. In some embodiments, the IL-22 dimer has an EC50 that is at least about 5× (including for example at least about 10×, 30×, 50×, 100×, 150×, 300×, 400×, 500×, 600×, 1000× or more) that of a wildtype monomeric IL-22 (for example the monomeric IL-22 having the sequence of SEQ ID NO: 3) in an in vitro cell proliferation assay. In some embodiments, the IL-22 dimer has an EC50 of no less than about 10 ng/mL (including for example no less than about any of 50 ng/mL, 100 ng/mL, 200 ng/mL, 300 ng/mL, 400 ng/mL, or more) in an in vitro STAT3 stimulation assay. In some embodiments, the IL-22 dimer has an EC50 that is at least about 10× (including for example at least about 50×, 100×, 200×, 300×, 400×, 500×, 600×, 700×, 800×, 900×, 1000×, 1500×, or more) that of a wildtype monomeric IL-22 (for example the monomeric IL-22 having the sequence of SEQ ID NO: 3) in an in vitro STAT3 stimulation assay.

In some embodiments, the IL-22 dimer has a serum half-life that is significantly longer than that of IL-22. In some embodiments, the IL-22 dimer as a serum half-life of at least about any of 15, 30, 50, 100, 150, 200, 250, 300, or 350 hours. In some embodiments, while the dose of IL-22 dimer is 2 µg/kg, the serum half-life is at least about any of 15, 30, 50, 100, 150, or 200 hours. In some embodiments, while the dose of IL-22 dimer is 10 µg/kg, the serum half-life is at least about any of 50, 100, 150, or 200 hours. In some embodiments, while the dose of IL-22 dimer is 30 µg/kg, the serum half-life is at least about any of 100, 150, 200, or 250 hours. In some embodiments, while the dose of IL-22 dimer is 45 µg/kg, the serum half-life is at least about any of 100, 150, 200, 250, 300, or 350 hours.

Preparation of IL-22 Dimers

The IL-22 monomeric subunits of the IL-22 dimers may be expressed using recombinant DNA technology. The nucleotide sequence encoding IL-22 monomeric subunits can be inserted into a replicable cloning or protein expression vector at restriction sites using known techniques. In some embodiments, a single nucleotide sequence encoding IL-22 monomeric subunits is inserted into a cloning or expression vector. In some embodiments, a nucleotide sequence encoding the IL-22 region and a nucleotide sequence encoding the extension peptide region may be separately inserted into a cloning or expression vector in such a manner that when the nucleotide sequence is expressed as a protein, a continuous polypeptide is formed. In some embodiments, a nucleotide sequence encoding a linker, a nucleotide sequence encoding a dimerization domain, and a nucleotide sequence encoding an IL-22 region may be separately inserted into a cloning or expression vector in such a manner that when the nucleotide sequence is expressed as a protein, a continuous polypeptide is formed. In some embodiments, the nucleotide sequence encoding IL-22 monomeric subunit may be fused to a nucleotide sequence encoding an affinity or identification tag, such as, but not limited to, a His-tag, FLAG-tag, SUMO-tag, GST-tag, antibody-tag, or MBP-tag. In some embodiments, the cloning or expression vector may be then transfected or transformed into eukaryotic or prokaryotic cells using known techniques. In some embodiments, IL-22 or IL-22 monomeric subunits may be expressed in vitro.

The expression host cell may be any cell able to express IL-22 dimers. Suitable prokaryotic expression host cells may include, but are not limited to, *Escherichia coli, Erwinia, Klebsiella, Proteus, Salmonella, Serratia, Shigella, Bacillus subtilis, Bacillus licheniformis, Pseudomonas,* and *Streptomyces*. Eukaryotic cell, such as fungi or yeast, may also be suitable for expression of IL-22 monomeric subunits, for example, but not limited to, *Saccharomyces, Schizosaccharomyces pombe, Kluyveromyces lactis, Kluyveromyces fragilis, Kluyveromyces waltii, Kluyveromyces drosophilarum, Kluyveromyces thermotolerans, Kluyveromyces marxianus, Pichia pastoris, Neurospora crassa, Schwanniomyces, Penicillium, Tolypocladium, Synechococcus* and *Aspergillus*. Plant or algal cells may also be suitable for expression of IL-22 monomeric subunits, such as *Chlamydomonas*. Eukaryotic cell derived from multicellular organisms may also be suitable for expression of IL-22 monomeric subunits, for example, but not limited to, invertebrate cells such as *Drosophila* S2 and *Spodoptera* Sf9, or mammalian cells such as Chinese Hamster Ovary (CHO) cells, COS cells, human embryonic kidney cells (such as HEK293 cells), murine testis trophoblastic cells, human lung cells, and murine breast cancer cells. After the IL-22 monomeric subunit cloning plasmid is transformed or transfected into a host cell, the host cells can be grown on conventional nutrient media and protein expression induced, if necessary. In some embodiments, the expression of IL-22 monomeric subunits do not require inducement.

In some embodiments, expressed IL-22 monomeric subunits will form IL-22 dimers. In some embodiments, IL-22 monomeric subunits will require further inducement, such as by supplying an oxidation compound (such as hydrogen peroxide or a catalytic metal), UV light, or a chemical crosslinker (such as formaldehyde, 1,6-bismaleimidohexane, 1,3-dibromo-2-propanol, bis(2-chloroethyl)sulfide, or glutaraldehyde).

In some embodiments, the forming of IL-22 dimers do not require inducement. In some embodiments, host cell used to express IL-22 dimers is China Hamster Ovary (CHO cell). In some embodiments, IL-22 dimers may be purified using any number of protein purification techniques. For example, IL-22 dimers may be purified using affinity chromatography, ion exchange chromatography, reverse-phase HPLC, size-exclusion chromatography, precipitation, or ultracentrifugation. In some embodiments, an affinity tag fused to the IL-22 monomeric subunit polypeptide may be removed.

The preparation methods of IL-22 dimers can be referred to the patent application PCT/CN2011/079124 filed by Generon (Shanghai) Corporation, LTD on Aug. 30, 2011, incorporated herein by reference.

Kits and Medicines

Also provided are kits and medicines suitable for any one of the methods described herein. For example, in some embodiments, there is provided a kit comprising an IL-22 dimer and an instruction for administering the IL-22 dimer intravenously, for example at a dosage of about 2 µg/kg to about 200 µg/kg (such as about 10 µg/kg to about 45 µg/kg). In some embodiments, there is provided a unit dosage form for intravenous administration, wherein the unit dosage form comprises an effective amount of IL-22 dimer that would allow administration of the IL-22 dimer at a dosage of about 2 µg/kg to about 200 µg/kg (such as about 10 µg/kg to about 45 µg/kg). In some embodiments, there is provided a medicine comprising IL-22 dimer for intravenous administration, wherein the medicine comprises an effective amount of IL-22 dimer that would allow administration of the IL-22 dimer at a dosage of about 2 μg/kg to about 200 μg/kg (such as about 10 μg/kg to about 45 μg/kg). In some embodiments, there is provided a use of IL-22 dimer for the manufacture of a medicament for treating a disease, wherein the medicament is suitable for intravenous administration, and wherein the medicament comprises an effective amount of IL-22 dimer that would allow administration of IL-22 at a dosage of about 2 μg/kg to about 200 μg/kg (such as about 10 μg/kg to about 45 μg/kg).

The kit, medicine, medicament, and article of manufacture described herein can be provided in the form of vials (such as sealed vials), IV bags, and syringes.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

The following exemplary embodiments further describe the present invention. Although the description referred to particular embodiments, it will be clear to one skilled in the art that the present invention may be practiced with variation of these specific details. Hence this invention should not be construed as limited to the embodiments set forth herein. Further, for the embodiments in which details of the experimental methods are not described, such methods are carried out according to conventional conditions such as those described in Sambrook et al. Molecular Cloning: A Laboratory Manual (New York: Cold Spring Harbor Laboratory Press, 1989), or as suggested by the manufacturers.

EXAMPLES

Example 1 Proliferation Effect of IL-22 or IL-22 Dimer on Colo205 Cells

Colo205 cells were cultured in RPMI1640 10% FBS medium and the cells were grown to the logarithmic phase. Supernatant was discarded and PBS was added to wash away residual culture medium, followed by addition of 2-5 mL 0.25% Trypsin-EDTA for digestion. Then medium was added and mixed to uniformity by pipetting. Mixture was centrifuged at 1500 rpm for 5 min and cells were collected and prepared into $5.0 \times 10^5$ cells/mL cell suspension with basic medium. The suspension was added into the wells of 96-well plate (100 pt/well) and stayed overnight at 37° C., in 5% $CO_2$ incubator. On the next day, the 96-well plate was removed from the $CO_2$ incubator and centrifuged at 800 rpm for 5 minutes at 4° C. Then, 90 μL of cell supernatant was withdrawn from each well and 90 μL 0.1% BSA/RPMI 1640 was added to each well, followed by addition of IL-22 dimer (consisting of two monomeric subunits each comprising a sequence shown in SEQ ID NO: 4) to the final concentration of 1.4, 4.1, 12.3, 37.0, 111.1, 333.3, 1000, 3000 ng/mL, IL-22 (rhIL-22, namely, recombinant human IL-22) to the final concentration of 0.01, 0.04, 0.12, 0.37, 1.1, 3.3, 10, 30 ng/mL. The mixture was incubated for 20 hours at 37° C. in 5% $CO_2$ incubator and cell supernatant was collected and the OD value thereof was tested using IL-10 ELISA kit (R&D, Cat: S1000B).

Figure 4:
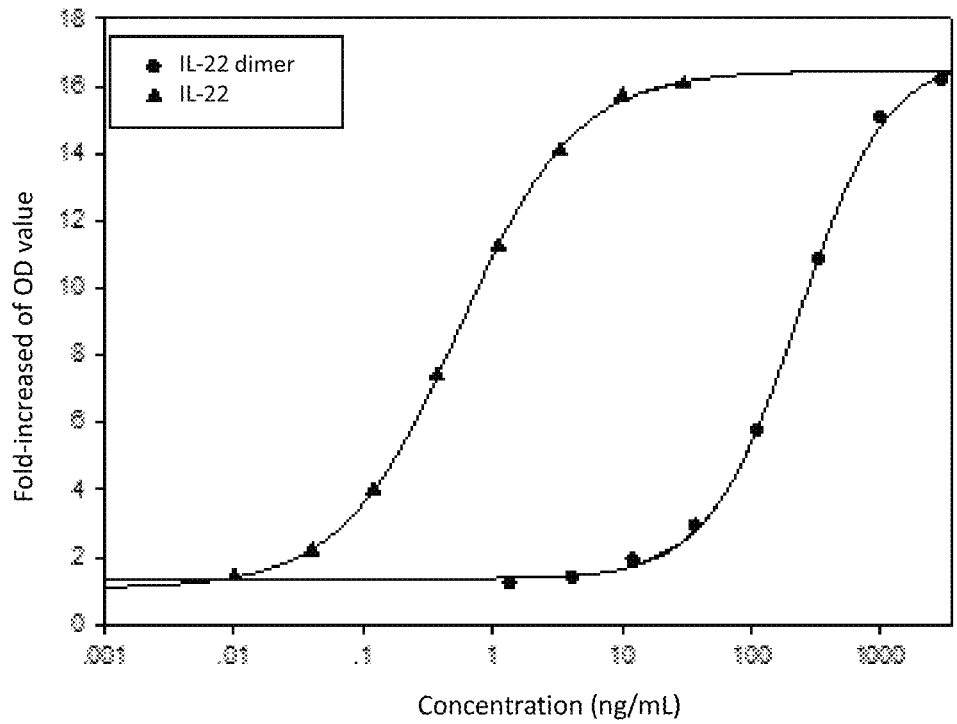
FIG. 4 shows the proliferative effect of IL-22 and IL-22 dimer on Colo205 cells in in vitro activity experiment.

As shown in FIG. 4, the half effective concentration (EC50) value of IL-22 dimer is 229 ng/mL (2,675 pM) and that of IL-22 is 0.54 ng/mL (32.4 pM). It shows that the bioactivity of IL-22 dimer is far lower than that of IL-22 monomer in in vitro activity experiment.

Example 2 Effect of IL-22 or IL-22 Dimer on STAT3 Activation in Colo205 Cells

Colo205 cells were cultured in RPMI1640 10% FBS medium and the cells were grown to the logarithmic phase. Supernatant was discarded and PBS was added to wash away residual culture medium, followed by addition of 2-5 mL 0.25% Trypsin-EDTA for digestion. Then medium was added and mixed to uniformity by pipetting. Mixture was centrifuged at 1500 rpm for 5 min and cells were collected and prepared into $2.0 \times 10^5$ Cell/ml cell suspension with basic medium RPMI1640. The suspension was added into the wells of 96-well plate (100 μL/well) and stayed at 37° C. for 6 hrs, in 5% $CO_2$ incubator. The suspension was treated respectively with various concentrations of rhIL-22 or IL-22 dimer (consisting of two monomeric subunits each comprising a sequence shown in SEQ ID NO: 4) for 1 hr. After discarding the supernatant, add 40 μL cell lysis buffer (Cat No. 9803S, Cell Signaling) into each well. The supernatant was collected by centrifugation. Protein concentration was determined using Bradford method. Additionally, STAT3 phosphorylation level was measured using an ELISA method (STAT3 [pY705] phosphor ELISA kit (Invitrogen, Cat: KH00481). The pSTAT3 content is calculated by dividing the detected concentration of pSTAT3 by protein concentration.

Figure 5:
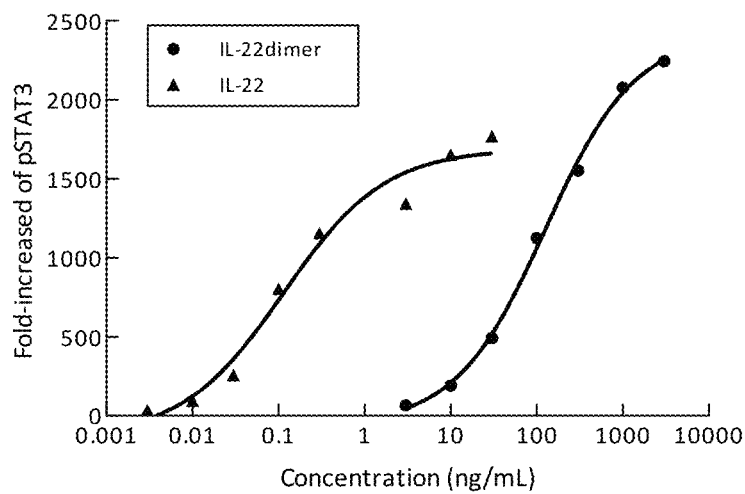
FIG. 5 shows the effect of IL-22 and IL-22 dimer on stimulating STAT3 in Colo205 cells in in vitro activity experiment.

As shown in FIG. 5, the half effective concentration (EC50) value of IL-22 dimer activating STAT3 is 119.5 ng/mL (1394 pM, calculated using the theoretical molecular weight of IL-22 dimer which is 85.7 I(D) and that of IL-22 is 0.14 ng/mL (6.9 pM, calculated using the molecular weight of IL-22 which is 16.71 D).

Example 3 Distribution of IL-22 Dimer in Organ Tissues in SD Rats

Figure 6:
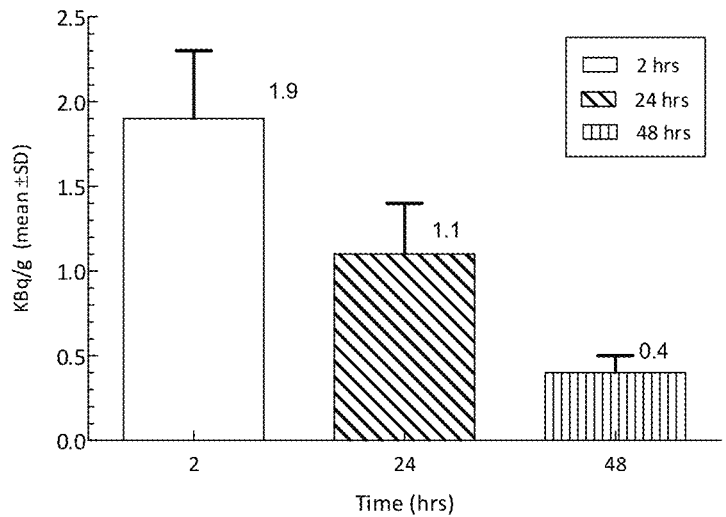
FIG. 6 shows the distribution of IL-22 dimer in pancreatic tissues in rats after administration. SD rats received a single intravenous injection of 30 μg/kg 125I labeled IL-22 dimer via cauda vein. The radioactivity counts in organ tissues were measured at 2, 24, and 48 hrs respectively after the injection.

18 SD rats were randomly divided into 3 groups with 6 animals per group(half male and half female). The animals received a tail vein injection of $^{125}$I-IL-22 dimer labeled by Iodogen method (consisting of two monomeric subunits each comprising a sequence shown in SEQ ID NO: 4) at a dose of 30 μg/kg. The animals were sacrificed at 2, 24 and 48 hrs after the injection, respectively. The organ tissues were collected and weighed, and the radioactivity counts were measured directly. Then the radioactivity counts per gram of tissues were calculated. The results showed that the IL-22 dimer was stable in pancreas for 48 hrs after the injection. As shown in FIG. 6, the concentrations of IL-22 dimer in pancreas at 24, 48 hrs were decreased to 56% and 21% of that of IL-22 dimer at 2 hrs after the injection, respectively. The concentrations of IL-22 dimer in livers at 24 hrs and 48 hrs were decreased to 28% and 9% of that of IL-22 dimer at 2 hrs after the injection, respectively. At 2 hrs after the injection, the concentrations of IL-22 dimer in pancreas were about 1/5 of that of IL-22 dimer in liver.

Example 4 Distribution of IL-22 Dimer in Organ Tissues in Cynomolgus Monkey 3 male cynomolgus monkeys, weighing 4.3-4.6 kg, received intravenous injection of IL-22 dimer (consisting of two monomeric subunits each comprising a sequence shown in SEQ ID NO: 4) at a dose of 100 μg/kg. The animals were sacrificed at 2 hrs after the injection. The organ tissues were collected and stored in liquid nitrogen. The tissues were weighed and lysed by adding the lysis buffer to obtain the tissue homogenate. After centrifugation, the supernatant was separated and subjected to protein concentration determination. The concentrations of IL-22 dimer in the tissues were measured using an ELISA method (Human IL-22 ELISA Kit, Biolegend, Cat. No. 434506).

Figure 7:
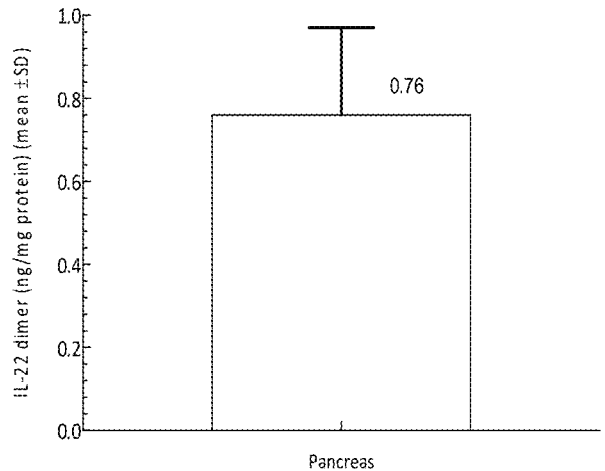
FIG. 7 shows the distribution of IL-22 dimer in pancreatic tissues in cynomolgus monkeys after administration. Cynomolgus monkeys received a single intravenous injection of 100 μg/kg IL-22 dimer. The drug concentrations in the organ tissues were measured at 2 hrs after the injection.

The results showed that the concentration of IL-22 dimer in the pancreas was fairly low (about 0.76 ng/mg protein). As shown in FIG. 7, this concentration was far lower than that of IL-22 dimer in liver(about 1/5 of the concentration in liver).

Example 5 Clinical Safety of IL-22 Dimer in Healthy Human Subject

Methods:

Healthy male volunteers were enrolled and randomized into 6 dose groups:

Placebo group (n=8): received a single dose of equal volume of 5% glucose/saline via intravenous infusion.

IL-22 dimer 2.0 μg/kg SC dose group (n=6) (SC group): received a single subcutaneous dose of IL-22 dimer at 2.0 μg/kg.

IL-22 dimer 2.0 μg/kg IV dose group (n=6) (IV group): IL-22 dimer were dissolved in 100 mL 5% glucose/saline solution and administered at a single dose of 2 μg/kg via intravenous infusion IL-22 dimer 10 μg/kg IV dose group (n=6) (IV group): IL-22 dimer were dissolved in 100 mL 5% glucose/saline solution and administered at a single dose of 10 μg/kg via intravenous infusion.

IL-22 dimer 30 μg/kg IV dose group (n=6) (IV group): IL-22 dimer were dissolved in 100 mL 5% glucose/saline solution and administered at a single dose of 30 μg/kg via intravenous infusion.

IL-22 dimer 45 μg/kg IV dose group (n=6) (IV group): IL-22 dimer were dissolved in 100 mL 5% glucose/saline solution and administered at a single dose of 45 μg/kg via intravenous infusion.

Wherein, the IL-22 dimer consisted of two monomeric subunits each comprising a sequence shown in SEQ ID NO: 4.

The safety was evaluated through physical examination, laboratory test, body weight, vital signs, electrocardiogram, and abdomen ultrasound, etc. In addition, the serum level of drug concentration, SAA-1, CRP, TG and cytokines were assayed.

Results:

A. Adverse Events

IL-22 dimer 2.0 μg/kg SC dose group: totally six adverse events considered related to the investigated drug, including injection site dry skin (×3), erythema (×2), and nummular eczema (×1).

IL-22 dimer 2.0 μg/kg IV dose group: no adverse events were observed.

IL-22 dimer 10 μg/kg IV dose group: two adverse events were observed, including chills (an infusion related reaction) (×1) and headache (×1).

IL-22 dimer 30 μg/kg IV dose group: six adverse events were observed, including local dry skin (×4), allergic dermatitis (×1), and infusion related reaction (×1).

IL-22 dimer 45 μg/kg IV dose group: twelve adverse events were observed, including local dry skin (×6), eye pruritus (×3), erythematous rash (×2), and somnolence (×1).

Placebo group: adverse events including upper respiratory tract infection (×1), lethargy (×1) and hyperhidrosis (×1) were observed.

The results of adverse events, physical examination, laboratory test, body weight, vital signs, electrocardiogram, and abdomen ultrasound data, etc, showed that a single intravenous administration of IL-22 dimer at a dose as high as 45 μg/kg demonstrated a good safety profile with no observed serious adverse events or life-threatening adverse events. Fewer adverse events were reported following IL-22 dimer dosing via IV compared to SC at the 2.0 μg/kg dose level, indicating that IV was much better tolerated by the study subjects (Table 2). The results demonstrated that intravenous administration of IL-22 dimer has a better safety and tolerability compared to subcutaneous administration.

TABLE 2

Adverse events at injection site and skin after IL-22 dimer administration

| Dosing group | Injection site | skin |
|---|---|---|
| placebo | Not observed | Not observed |
| 2 μg/kg, SC | dry skin (×3), erythema (×2), and nummular eczema (×1) were observed 10-17 days after the administration | Not observed |
| 2 μg/kg, IV | Not observed | Not observed |
| 10 μg/kg, IV | Not observed | Not observed |
| 30 μg/kg, IV | Not observed | Local dry skin (×4), allergic dermatitis (×1) |
| 45 μg/kg, IV | Not observed | Local dry skin (×6), eye pruritus (×3), erythematous rash (×2) |

B. Pharmacokinetics of IL-22 Dimer in Human

The vein blood samples were taken prior to the administration and at different time points following the administration. After centrifugation, the serum was separated and stored at <70° C. The drug concentration in the serum was measured using an ELISA method (Human IL-22 ELISA Kit, Biolegend, Cat. No. 434506). Pharmacokinetic parameters were analyzed using a non-compartmental model on the detected results (analysis software: Phoenix™ WinNonlin® (Pharsight Corporation, Version 6.2.1). The results showed IL-22 dimer had a very excellent half-life in human, among which, the single dose of 45 μg/kg group had a half-life of 206 hrs which was significantly better than that of IL-22 monomer.

TABLE 3

Pharmacokinetic parameters (mean value, n = 6)

| Dosage (μg/kg, IV) | $T_{max}$ (hrs) | $C_{max}$ (ng/mL) | $T_{last}$ (hrs) | $C_{last}$ (ng/mL) | $AUC_{0-t}$ (hr*ng/mL) | $AUC_{0-\infty}$ (hr*ng/mL) | $AUC_{0-24\,h}$ (hr*ng/mL) | $T_{1/2}$ (hrs) | Cl (mL/hr/kg) | Vz (mL/kg) |
|---|---|---|---|---|---|---|---|---|---|---|
| 2  | 0.7 | 15.5 | 60  | 3.75 | 437   | 650   | 247  | 39.4 | 3.35 | 177 |
| 10 | 0.2 | 62.3 | 284 | 4.41 | 4150  | 4840  | 1050 | 108  | 2.15 | 330 |
| 30 | 0.2 | 176  | 528 | 6.12 | 15400 | 16900 | 3230 | 161  | 1.82 | 419 |
| 45 | 0.2 | 247  | 528 | 7.73 | 18000 | 20400 | 4340 | 206  | 2.26 | 654 |

C. IL-22 Dimer can Significantly Increase the Serum Levels of SAA, CRP and Decrease Serum Levels of TG a. Serum Amyloid Protein (SAA)

The concentration of serum SAA-1 was measured using an ELISA method (human SAA ELISA kit, Cat. No. KHA0011C, Invitrogen).

Figure 8A:
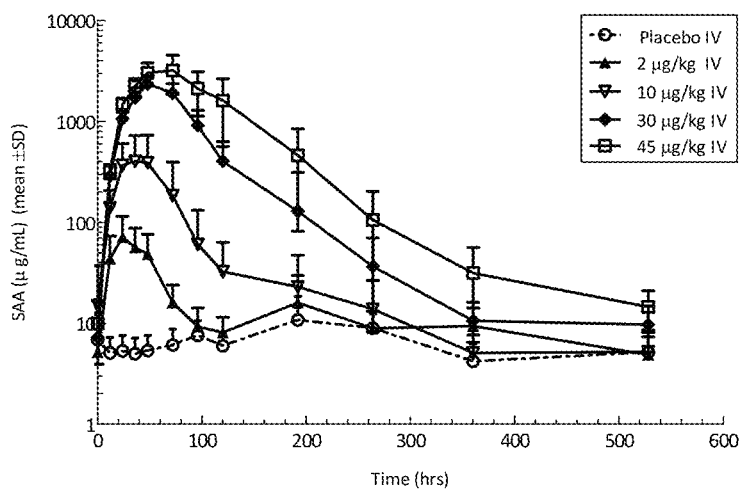
FIG. 8A shows the changes of the serum levels of amyloid protein (SAA) in human with the time after intravenous administration of IL-22 dimer.

The results showed the IV administration of IL-22 dimer can significantly increase the human serum concentration of SAA, indicating a very significant biological activity. As shown in FIG. 8A, compared to the placebo group, the concentration of SAA-1 was significantly increased at 12 hrs after the IL-22 dimer administration. High serum concentration of SAA remain fairly high in the 45 μg/kg dose group on day 15 after the administration.

TABLE 4 the maximum concentration (Cmax) and fold-increased of SAA-1

| Group (IV) | SAA-1 Cmax (μg/kg) | Fold-increased of Cmax (relative to placebo group) |
|---|---|---|
| Placebo | 6* | 1 |
| IL-22 dimer 2 μg/kg, IV | 71 | 12 |
| IL-22 dimer 10 μg/kg, IV | 402 | 67 |
| IL-22 dimer 30 μg/kg, IV | 2355 | 393 |
| IL-22 dimer 45 μg/kg, IV | 3194 | 532 |

*indicating average value of placebo group b. C-Reactive Protein

The levels of C-reactive protein (CRP) were measured using immunity transmission turbidity.

Figure 8B:
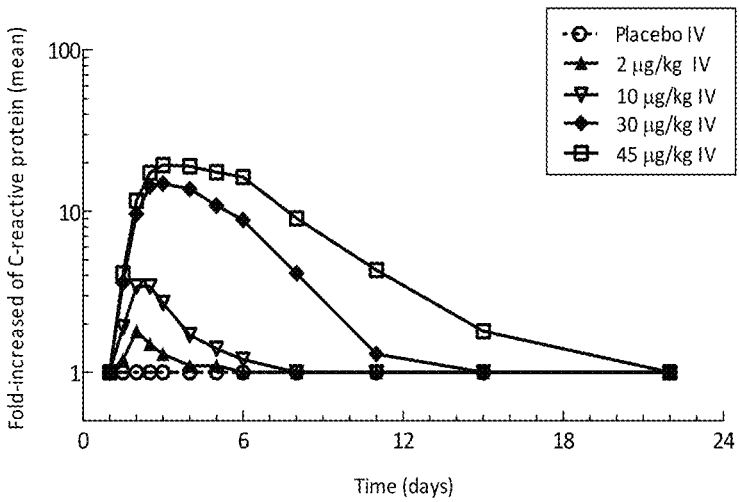
FIG. 8B shows the changes of the serum levels of C-reactive protein in human with the time after intravenous administration of IL-22 dimer.

As shown in FIG. 8B, the IV administration of IL-22 dimer significantly increased the serum concentration of C-reactive protein compared to the placebo group.

c. Triglyceride

The changes of serum triglycerides prior to and post the administration were detected using automatic blood biochemistry analyzer.

Figure 8C:
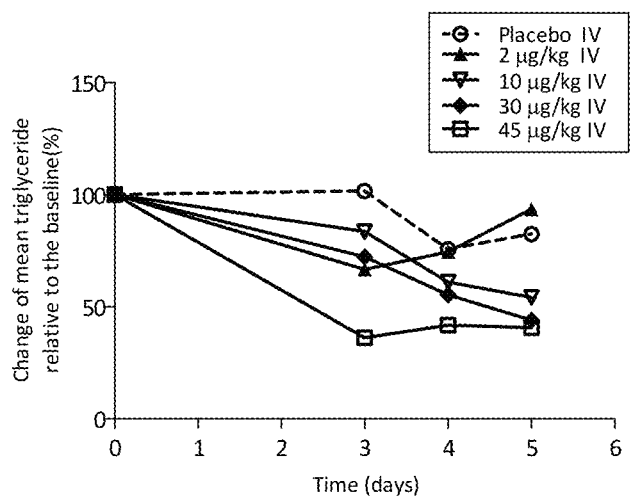
FIG. 8C shows the changes of the serum levels of triglyceride in human with the time after intravenous administration of IL-22 dimer.

As shown in FIG. 8C, the IV administration of IL-22 dimer significantly reduced the serum levels of triglyceride, exhibiting an obvious dose response relationship compared to the placebo group.

d. Cytokine Assay

The serum samples of placebo group and IL-22 dimer 45 μg/kg IV group were collected before the administration and at 24, 48 hrs after the administration, and were measured using Proteome Profiler Arrays-Human Cytokine Array Panel A (Cat. No. ARY005, R&D systems) to obtain the levels of various cytokines. The PBMCs (human Peripheral Blood Mononuclear Cells) were treated with 50 ng/mL PMA (phorbol myristate acetate) for 24 hrs and then the supernatant was used as a positive control. 200 μL of each serum samples was loaded and measured following the kit's instruction.

Figure 8D:
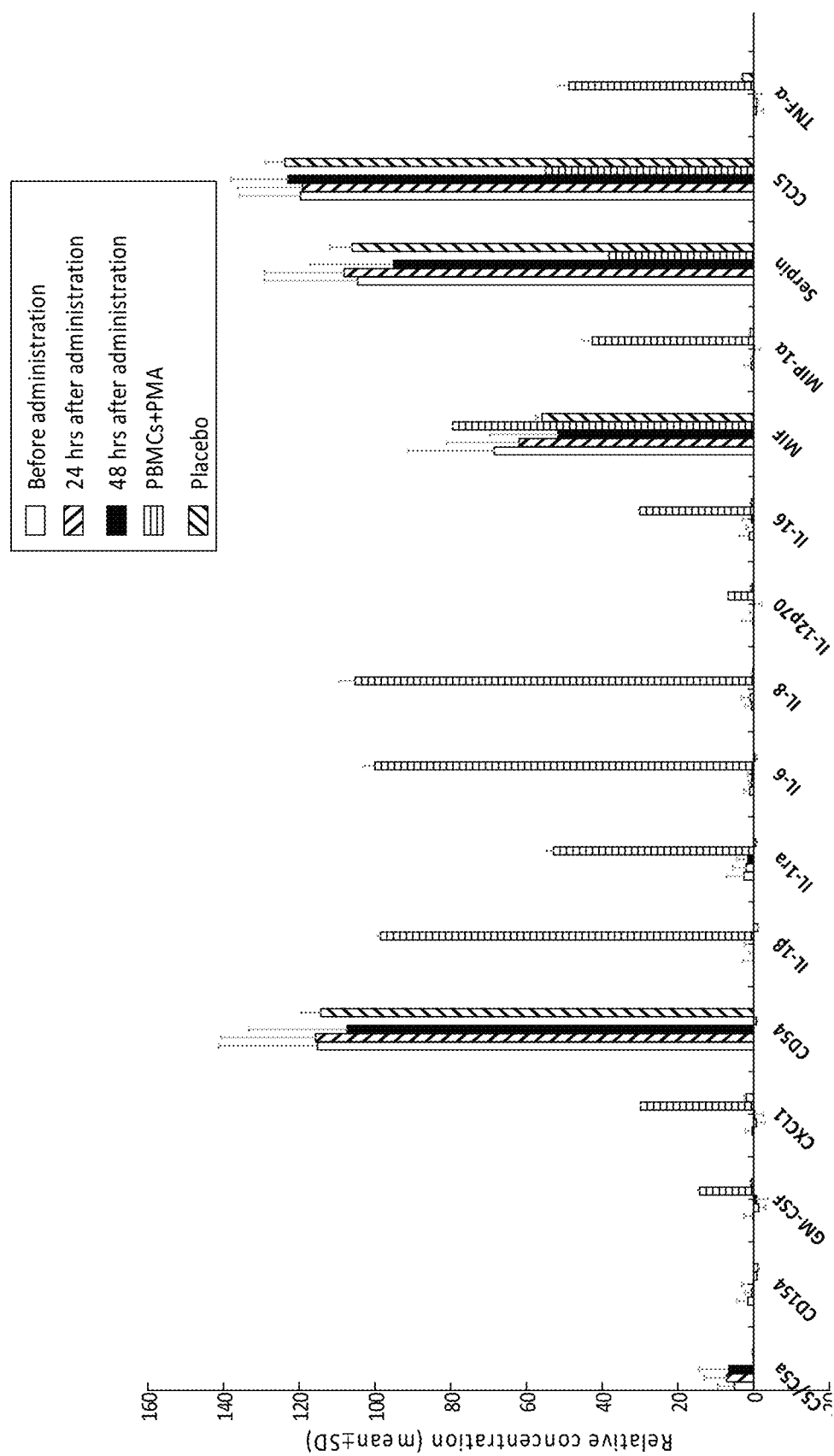
FIG. 8D shows the effect on the serum levels of various cytokines in human with the time after intravenous administration of IL-22 dimer.

As shown in FIG. 8D, the levels of inflammatory cytokines such as TNFα, IL-6, IL-1β, IL-8, etc. were markedly increased in the positive control (PBMCs+PMA). Showing a similar profile to the placebo group, the levels of CD54, MIF, Serpin E1 and CCL5 were relatively higher for the serum samples taken at 24 and 48 hrs after the administration in the IL-22 dimer 45 μg/kg IV group, and the levels of inflammatory cytokines such as TNFα, IL-6, IL-1l3, IL-8 did not markedly change compared to that of serum samples taken prior to the administration. These demonstrated that the administration of IL-22 dimer does not lead to increased levels of serum inflammatory cytokines.

Example 6 Preventive and Therapeutic Efficacy of IL-22 or IL-22 Dimer in Rat Model of Acute Pancreatitis Induced by Retrograde Injection of Sodium Taurocholate into the Biliopancreatic Duct Acute pancreatitis model induced by retrograde injection of sodium taurocholate into the biliopancreatic duct, has been widely used to assess the pathogenesis of bile reflux pancreatitis and the efficacy of a medicament. In this experiment, the rat model of acute pancreatitis was produced by retrograde injection of 0.1 mL/100 g 3.5% sodium taurocholate into the biliopancreatic duct.

SD rats were randomly divided into 3 groups:

Model control group(n=6), received a single intravenous injection of equal volume of solvent two hrs before surgery.

IL-22 monomer 40 μg/kg group (n=7), received a single intravenous injection of 40 μg/kg recombinant human IL-22 (rhIL-22) two hrs before surgery.

IL-22 dimer 100 μg/kg group (n=7), received a single intravenous injection of 100 μg/kg IL-22 dimer (comprising an equal molar IL-22 molecule dosage in comparison to IL-22 monomer 40 μg/kg group) two hrs before surgery.

The IL-22 dimer consisted of two monomeric subunits each comprising a sequence shown in SEQ ID NO: 4.

The animals were given free access to water and fasted for 12 hrs before surgery.

Surgical Procedures:

Rats in the model group were anaesthetized with diethyl ether. The abdomen was opened by a midline incision, the duodenum and common bile duct were identified, then the common bile duct was temporarily occluded at the confluence of hepatic hilus hepatic duct using a microvascular clamp. Upon finding a mesenterium avascular area at lateral wall of duodenum, a 0.4 size needle was used to puncture and sideling insert into the bile-pancreatic duct in the mesenterium avascular area, and then pulled out. A polyethylene (PE) 10 tube was then inserted into the bile-pancreatic duct along the duodenal papilla for 8-10 mm via the hole, and fixed to avoid dropping out. 3.5% sodium taurocholate (0.1 mL/100 g) was slowly infused in a retrograde way, and the needle core was kept staying for 8 mins after injection. Upon removing the polyethylene tube and microvascular clamp, the abdomen was closed. Rats were given free access to food and water after surgery. At 12 hrs after surgery, blood samples were taken from rat orbital venous plexus, and then the serum was separated by centrifuging. The serum levels of amylase and lipase were measured.

The animals were sacrificed 48 hrs after surgery. The pancreas tissues of rats were taken and fixed in 10% formalin solution. Tissues at head, middle, and tail of the pancreas were sliced and made into 3 μm paraffin sections, respectively. The sections were stained with HE, and the pathological changes were observed under a light microscope. Scores of edema, necrosis, hemorrhage, inflammatory cell infiltration, etc were evaluated in a double blind fashion, according to the scales of Schmidt (Schmidt et al. Ann Surg, 1992, 215(1):44-56). Scoring of 3 sections including the head, middle, and tail of the pancreas for each rat was performed.

Figure 9A:
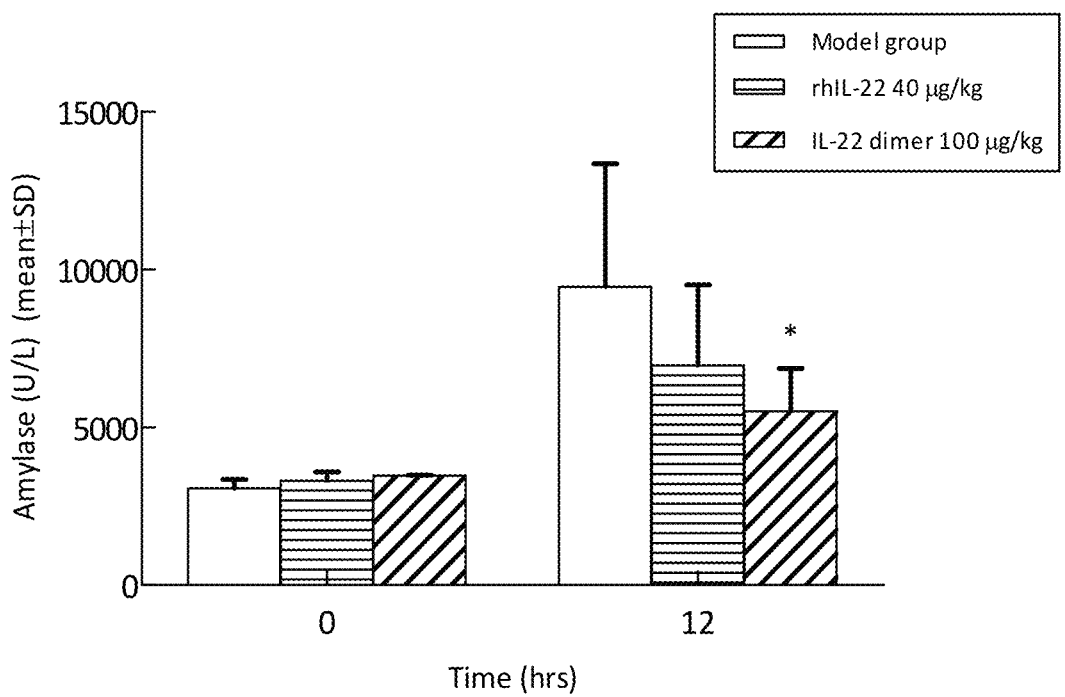
FIG. 9A shows the effect of IL-22 and IL-22 dimer on serum amylase levels in pancreatitis model rats.
Figure 9B:
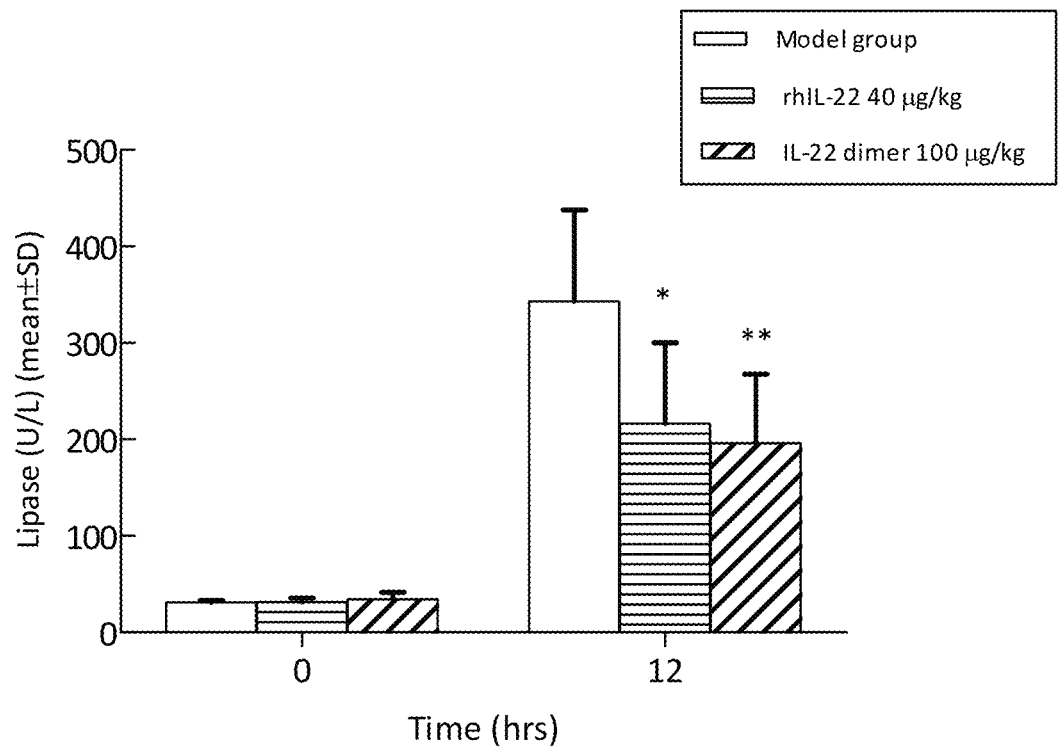
FIG. 9B shows the effect of IL-22 and IL-22 dimer on serum lipase levels in pancreatitis model rats.

Results:

The pancreatitis animal model was successfully established, as evidenced by a significant elevation in serum levels of amylase and lipase. As shown in FIGS. 9A and 9B, compared to the model group, IL-22 monomer has a trend to decrease the serum levels of amylase, but there was no significant difference. The serum levels of amylase were significantly decreased after the IL-22 dimer treatment (P=0.03). Compared to the model group, the serum levels of lipase were significantly decreased (P=0.03) after the IL-22 monomer treatment, whereas the serum levels of lipase were significantly decreased after the IL-22 dimer treatment (P=0.008). It is worth noting that, at equal molar IL-22 dosage, the IL-22 dimer was therapeutically effective in pancreatitis rat model, and the efficacy was better than that of IL-22. Under a microscope, obvious edema, a mass of inflammatory cell infiltration, necrosis of partial acinar cell and adipose cell, and a small amount of hemorrhage were observed in the pancreatic tissues of model group. IL-22 dimer can significantly improve the pathology score in animals of pancreatitis, showing a protective role on pancreas. At equal molar IL-22 dosage, no significant protective effect of IL-22 monomer on pancreas was observed.

TABLE 5

The pathology scores of pancreatic tissue in rats

| | Edema | Inflammatory cell infiltration | Necrosis of acinar cell | Hemorrhage | Necrosis of adipose cell | Total |
|---|---|---|---|---|---|---|
| Model group | 6.2 ± 1.8 | 7.0 ± 1.2 | 3.8 ± 2.2 | 2.4 ± 2.1 | 1.4 ± 0.9 | 20.8 ± 4.0 |
| IL-22 monomer group 40 μg/kg | 7.4 ± 1.7 | 5.7 ± 1.6 | 2.4 ± 1.7 | 3.7 ± 3.4 | 0.9 ± 0.7 | 20.1 ± 4.0 |
| IL-22 dimer group 100 μg/kg | 4.3 ± 2.7 [b] | 5.7 ± 2.3 | 2.3 ± 0.5 | 2.3 ± 2.1 | 0.5 ± 0.8 | 15.2 ± 3.8 [a,b] |

[a] indicating P <0.05 compared to the model group.
[b] indicating P <0.05 compared to the IL-22 monomer group.

All references mentioned in the present invention are incorporated herein by reference as if each of those references has been incorporated by reference individually. Although the description referred to particular embodiments, it will be clear to a person skilled in the art that the present invention may be practiced with variation of these specific details. Hence this invention should not be construed as limited to the embodiments set forth herein.

We claim:

1. A method of treating a disease in a human individual, comprising intravenously administering to the human individual an effective amount of an IL-22 dimer, wherein the amount of the IL-22 dimer is about 2 µg/kg to about 200 µg/kg, wherein the IL-22 dimer comprises two monomeric subunits, wherein each monomeric subunit comprises an IL-22 domain and a dimerization domain, wherein the dimerization domain comprises the CH2 and CH3 domains of human IgG, and wherein the disease is liver disease, Parkinson's disease, or stroke.

2. The method of claim 1, wherein the IL-22 dimer is administered at the amount of about 5 µg/kg to about 80 µg/kg.

3. The method of claim 1, wherein the IL-22 dimer is administered at the amount of about 10 µg/kg to about 45 µg/kg.

4. The method of claim 1, wherein the IL-22 dimer is administered no more than once a week.

5. The method of claim 1, wherein the IL-22 dimer is administered no more than once a month.

6. The method of claim 1, wherein the IL-22 dimer is administered no more than once every three months.

7. The method of claim 1, wherein each monomeric subunit comprises the IL-22 domain linked to the dimerization domain via an optional linker sequence.

8. The method of claim 7, wherein the linker sequence is about 6 to about 30 amino acids in length.

9. The method of claim 8, wherein the linker sequence comprises the sequence of SEQ ID NO: 1 or 10.

10. The method of claim 1, wherein the dimerization domain comprises at least two cysteines capable of forming intermolecular disulfide bonds.

11. The method of claim 1, wherein the dimerization domain comprises the sequence of SEQ ID NO: 2 or 9.

12. The method of claim 1, wherein the IL-22 domain of each monomeric subunit comprises the sequence of SEQ ID NO: 3.

13. The method of claim 1, wherein each monomeric subunit comprises an amino acid sequence selected from the group consisting of SEQ ID NOs: 4 and 6-8.

14. The method of claim 1, wherein the IL-22 domain is fused to the N-terminus of the dimerization domain within each monomeric subunit.

15. The method of claim 1, wherein the IgG is IgG2 or IgG4.

16. The method of claim 1, wherein the IL-22 dimer is administered at the amount of about 2 µg/kg to about 45 µg/kg.

17. The method of claim 1, wherein the liver disease is viral hepatitis.

18. The method of claim 1, wherein the liver disease comprises liver damage and/or liver inflammation.

19. The method of claim 1, wherein the liver disease is selected from the group consisting of cirrhosis, liver failure, hepatitis, non-alcoholic steatohepatitis, and fatty liver.

* * * * *

SEQUENCE LISTING

```
<160> NUMBER OF SEQ ID NOS: 10

<210> SEQ ID NO 1
<211> LENGTH: 16
<212> TYPE: PRT
<213> ORGANISM: Artificial sequence
<220> FEATURE:
<223> OTHER INFORMATION: short peptide

<400> SEQUENCE: 1

Gly Ser Gly Gly Gly Ser Gly Gly Gly Ser Gly Gly Gly Gly Ser
1               5                   10                  15

<210> SEQ ID NO 2
<211> LENGTH: 223
<212> TYPE: PRT
<213> ORGANISM: Artificial sequence
<220> FEATURE:
<223> OTHER INFORMATION: IgG2 Fc

<400> SEQUENCE: 2
```

-continued

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
        210                 215                 220

<210> SEQ ID NO 3
<211> LENGTH: 146
<212> TYPE: PRT
<213> ORGANISM: Artificial sequence
<220> FEATURE:
<223> OTHER INFORMATION: IL-22

<400> SEQUENCE: 3

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

```
Cys Ile
145

<210> SEQ ID NO 4
<211> LENGTH: 385
<212> TYPE: PRT
<213> ORGANISM: Artificial sequence
<220> FEATURE:
<223> OTHER INFORMATION: IL-22 -linker -IgG2 Fc

<400> SEQUENCE: 4

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Gly Ser Gly Gly Ser Gly Gly Gly Ser Gly Gly Gly
145                 150                 155                 160

Gly Ser Val Glu Cys Pro Pro Cys Pro Ala Pro Pro Val Ala Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Gln Phe Asn Trp Tyr Val Asp Gly Val Glu Val His Asn
    210                 215                 220

Ala Lys Thr Lys Pro Arg Glu Glu Gln Phe Asn Ser Thr Phe Arg Val
225                 230                 235                 240

Val Ser Val Leu Thr Val Val His Gln Asp Trp Leu Asn Gly Lys Glu
                245                 250                 255

Tyr Lys Cys Lys Val Ser Asn Lys Gly Leu Pro Ala Ser Ile Glu Lys
            260                 265                 270

Thr Ile Ser Lys Thr Lys Gly Gln Pro Arg Glu Pro Gln Val Tyr Thr
        275                 280                 285

Leu Pro Pro Ser Arg Glu Glu Met Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Met Leu
                325                 330                 335

Asp Ser Asp Gly Ser Phe Phe Leu Tyr Ser Lys Leu Thr Val Asp Lys
            340                 345                 350
```

Ser Arg Trp Gln Gln Gly Asn Val Phe Ser Cys Ser Val Met His Glu
            355                 360                 365

Ala Leu His Asn His Tyr Thr Gln Lys Ser Leu Ser Leu Ser Pro Gly
        370                 375                 380

Lys
385

<210> SEQ ID NO 5
<211> LENGTH: 308
<212> TYPE: PRT
<213> ORGANISM: Artificial sequence
<220> FEATURE:
<223> OTHER INFORMATION: IL-22 -linker -IL-22

<400> SEQUENCE: 5

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Gly Ser Gly Gly Gly Ser Gly Gly Gly Gly Ser Gly Gly Gly
145                 150                 155                 160

Gly Ser Ala Pro Ile Ser Ser His Cys Arg Leu Asp Lys Ser Asn Phe
                165                 170                 175

Gln Gln Pro Tyr Ile Thr Asn Arg Thr Phe Met Leu Ala Lys Glu Ala
            180                 185                 190

Ser Leu Ala Asp Asn Asn Thr Asp Val Arg Leu Ile Gly Glu Lys Leu
        195                 200                 205

Phe His Gly Val Ser Met Ser Glu Arg Cys Tyr Leu Met Lys Gln Val
    210                 215                 220

Leu Asn Phe Thr Leu Glu Glu Val Leu Phe Pro Gln Ser Asp Arg Phe
225                 230                 235                 240

Gln Pro Tyr Met Gln Glu Val Val Pro Phe Leu Ala Arg Leu Ser Asn
                245                 250                 255

Arg Leu Ser Thr Cys His Ile Glu Gly Asp Asp Leu His Ile Gln Arg
            260                 265                 270

Asn Val Gln Lys Leu Lys Asp Thr Val Lys Lys Leu Gly Glu Ser Gly
        275                 280                 285

Glu Ile Lys Ala Ile Gly Glu Leu Asp Leu Leu Phe Met Ser Leu Arg
    290                 295                 300

Asn Ala Cys Ile
305

```
<210> SEQ ID NO 6
<211> LENGTH: 375
<212> TYPE: PRT
<213> ORGANISM: Artificial sequence
<220> FEATURE:
<223> OTHER INFORMATION: IL-22-linker-IgG2 Fc

<400> SEQUENCE: 6
```

| | | | | | | | | | | | | | | |
|---|---|---|---|---|---|---|---|---|---|---|---|---|---|---|
| Ala | Pro | Ile | Ser | Ser | His | Cys | Arg | Leu | Asp | Lys | Ser | Asn | Phe | Gln | Gln |
| 1 | | | | 5 | | | | | 10 | | | | | 15 | |
| Pro | Tyr | Ile | Thr | Asn | Arg | Thr | Phe | Met | Leu | Ala | Lys | Glu | Ala | Ser | Leu |
| | | | 20 | | | | | 25 | | | | | 30 | | |
| Ala | Asp | Asn | Asn | Thr | Asp | Val | Arg | Leu | Ile | Gly | Glu | Lys | Leu | Phe | His |
| | | 35 | | | | | 40 | | | | | 45 | | | |
| Gly | Val | Ser | Met | Ser | Glu | Arg | Cys | Tyr | Leu | Met | Lys | Gln | Val | Leu | Asn |
| 50 | | | | | 55 | | | | | 60 | | | | | |
| Phe | Thr | Leu | Glu | Glu | Val | Leu | Phe | Pro | Gln | Ser | Asp | Arg | Phe | Gln | Pro |
| 65 | | | | | 70 | | | | | 75 | | | | | 80 |
| Tyr | Met | Gln | Glu | Val | Val | Pro | Phe | Leu | Ala | Arg | Leu | Ser | Asn | Arg | Leu |
| | | | | 85 | | | | | 90 | | | | | 95 | |
| Ser | Thr | Cys | His | Ile | Glu | Gly | Asp | Asp | Leu | His | Ile | Gln | Arg | Asn | Val |
| | | | 100 | | | | | 105 | | | | | 110 | | |
| Gln | Lys | Leu | Lys | Asp | Thr | Val | Lys | Lys | Leu | Gly | Glu | Ser | Gly | Glu | Ile |
| | | | 115 | | | | | 120 | | | | | 125 | | |
| Lys | Ala | Ile | Gly | Glu | Leu | Asp | Leu | Leu | Phe | Met | Ser | Leu | Arg | Asn | Ala |
| | | 130 | | | | | 135 | | | | | 140 | | | |
| Cys | Ile | Ala | Ser | Thr | Lys | Gly | Pro | Val | Glu | Cys | Pro | Pro | Cys | Pro | Ala |
| 145 | | | | | 150 | | | | | 155 | | | | | 160 |
| Pro | Pro | Val | Ala | Gly | Pro | Ser | Val | Phe | Leu | Phe | Pro | Pro | Lys | Pro | Lys |
| | | | | 165 | | | | | 170 | | | | | 175 | |
| Asp | Thr | Leu | Met | Ile | Ser | Arg | Thr | Pro | Glu | Val | Thr | Cys | Val | Val | Val |
| | | | 180 | | | | | 185 | | | | | 190 | | |
| Asp | Val | Ser | His | Glu | Asp | Pro | Glu | Val | Gln | Phe | Asn | Trp | Tyr | Val | Asp |
| | | 195 | | | | | 200 | | | | | 205 | | | |
| Gly | Val | Glu | Val | His | Asn | Ala | Lys | Thr | Lys | Pro | Arg | Glu | Glu | Gln | Phe |
| | 210 | | | | | 215 | | | | | 220 | | | | |
| Asn | Ser | Thr | Phe | Arg | Val | Val | Ser | Val | Leu | Thr | Val | Val | His | Gln | Asp |
| 225 | | | | | 230 | | | | | 235 | | | | | 240 |
| Trp | Leu | Asn | Gly | Lys | Glu | Tyr | Lys | Cys | Lys | Val | Ser | Asn | Lys | Gly | Leu |
| | | | | 245 | | | | | 250 | | | | | 255 | |
| Pro | Ala | Ser | Ile | Glu | Lys | Thr | Ile | Ser | Lys | Thr | Lys | Gly | Gln | Pro | Arg |
| | | | 260 | | | | | 265 | | | | | 270 | | |
| Glu | Pro | Gln | Val | Tyr | Thr | Leu | Pro | Pro | Ser | Arg | Glu | Glu | Met | Thr | Lys |
| | | | 275 | | | | | 280 | | | | | 285 | | |
| Asn | Gln | Val | Ser | Leu | Thr | Cys | Leu | Val | Lys | Gly | Phe | Tyr | Pro | Ser | Asp |
| | | 290 | | | | | 295 | | | | | 300 | | | |
| Ile | Ala | Val | Glu | Trp | Glu | Ser | Asn | Gly | Gln | Pro | Glu | Asn | Asn | Tyr | Lys |
| 305 | | | | | 310 | | | | | 315 | | | | | 320 |
| Thr | Thr | Pro | Pro | Met | Leu | Asp | Ser | Asp | Gly | Ser | Phe | Phe | Leu | Tyr | Ser |
| | | | | 325 | | | | | 330 | | | | | 335 | |
| Lys | Leu | Thr | Val | Asp | Lys | Ser | Arg | Trp | Gln | Gln | Gly | Asn | Val | Phe | Ser |
| | | | 340 | | | | | 345 | | | | | 350 | | |
| Cys | Ser | Val | Met | His | Glu | Ala | Leu | His | Asn | His | Tyr | Thr | Gln | Lys | Ser |
| | | | 355 | | | | | 360 | | | | | 365 | | |

Leu Ser Leu Ser Pro Gly Lys
    370             375

<210> SEQ ID NO 7
<211> LENGTH: 385
<212> TYPE: PRT
<213> ORGANISM: Artificial sequence
<220> FEATURE:
<223> OTHER INFORMATION: IgG2 Fc-linker- IL-2

<400> SEQUENCE: 7

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys Gly
    210                 215                 220

Ser Gly Gly Gly Ser Gly Gly Gly Ser Gly Gly Gly Ser Ala
225                 230                 235                 240

Pro Ile Ser Ser His Cys Arg Leu Asp Lys Ser Asn Phe Gln Gln Pro
                245                 250                 255

Tyr Ile Thr Asn Arg Thr Phe Met Leu Ala Lys Glu Ala Ser Leu Ala
            260                 265                 270

Asp Asn Asn Thr Asp Val Arg Leu Ile Gly Glu Lys Leu Phe His Gly
        275                 280                 285

Val Ser Met Ser Glu Arg Cys Tyr Leu Met Lys Gln Val Leu Asn Phe
    290                 295                 300

Thr Leu Glu Glu Val Leu Phe Pro Gln Ser Asp Arg Phe Gln Pro Tyr
305                 310                 315                 320

Met Gln Glu Val Val Pro Phe Leu Ala Arg Leu Ser Asn Arg Leu Ser
                325                 330                 335

Thr Cys His Ile Glu Gly Asp Asp Leu His Ile Gln Arg Asn Val Gln
            340                 345                 350

```
Lys Leu Lys Asp Thr Val Lys Leu Gly Glu Ser Gly Glu Ile Lys
            355                 360                 365

Ala Ile Gly Glu Leu Asp Leu Leu Phe Met Ser Leu Arg Asn Ala Cys
370                 375                 380

Ile
385

<210> SEQ ID NO 8
<211> LENGTH: 375
<212> TYPE: PRT
<213> ORGANISM: Artificial sequence
<220> FEATURE:
<223> OTHER INFORMATION: IgG2 Fc-linker- IL-22

<400> SEQUENCE: 8

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys Ala
    210                 215                 220

Ser Thr Lys Gly Pro Ala Pro Ile Ser Ser His Cys Arg Leu Asp Lys
225                 230                 235                 240

Ser Asn Phe Gln Gln Pro Tyr Ile Thr Asn Arg Thr Phe Met Leu Ala
                245                 250                 255

Lys Glu Ala Ser Leu Ala Asp Asn Asn Thr Asp Val Arg Leu Ile Gly
            260                 265                 270

Glu Lys Leu Phe His Gly Val Ser Met Ser Glu Arg Cys Tyr Leu Met
        275                 280                 285

Lys Gln Val Leu Asn Phe Thr Leu Glu Glu Val Leu Phe Pro Gln Ser
    290                 295                 300

Asp Arg Phe Gln Pro Tyr Met Gln Glu Val Val Pro Phe Leu Ala Arg
305                 310                 315                 320
```

```
Leu Ser Asn Arg Leu Ser Thr Cys His Ile Glu Gly Asp Asp Leu His
            325                 330                 335

Ile Gln Arg Asn Val Gln Lys Leu Lys Asp Thr Val Lys Lys Leu Gly
            340                 345                 350

Glu Ser Gly Glu Ile Lys Ala Ile Gly Glu Leu Asp Leu Leu Phe Met
            355                 360                 365

Ser Leu Arg Asn Ala Cys Ile
            370                 375

<210> SEQ ID NO 9
<211> LENGTH: 228
<212> TYPE: PRT
<213> ORGANISM: homo sapiens

<400> SEQUENCE: 9

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
        130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
        210                 215                 220

Ser Pro Gly Lys
225

<210> SEQ ID NO 10
<211> LENGTH: 6
<212> TYPE: PRT
<213> ORGANISM: Artificial sequence
<220> FEATURE:
<223> OTHER INFORMATION: short peptide

<400> SEQUENCE: 10

Ala Ser Thr Lys Gly Pro
1               5
```